(12) United States Patent
Howell et al.

(10) Patent No.: US 6,642,196 B2
(45) Date of Patent: *Nov. 4, 2003

(54) METHOD OF DELIVERING A BENEFIT AGENT

(75) Inventors: Steven Howell, Sharnbrook (GB); Julie Little, Sharnbrook (GB); Cornelis Paul Van Der Logt, Vlaardingen (NL); Neil James Parry, Sharnbrook (GB)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 88 days.

This patent is subject to a terminal disclaimer.

(21) Appl. No.: 09/742,689

(22) Filed: Dec. 20, 2000

(65) Prior Publication Data

US 2001/0039250 A1 Nov. 8, 2001

(30) Foreign Application Priority Data

Dec. 22, 1999 (EP) .............................. 99310430

(51) Int. Cl.⁷ .............................. C12S 9/00; C11D 9/42; C11D 17/08

(52) U.S. Cl. .................. 510/392; 510/119; 510/122; 510/130; 510/138; 510/137; 510/141; 510/151; 510/158; 510/159; 510/372; 510/283; 510/286; 510/299; 510/300; 510/302; 510/303; 510/305; 510/308; 510/343; 510/374; 510/394; 510/375; 510/379; 510/380

(58) Field of Search ................... 510/119, 122, 510/130, 138, 137, 141, 151, 158, 159, 372, 283, 286, 299, 300, 302, 303, 305, 308, 342, 343, 374, 394, 375, 380, 379

(56) References Cited

U.S. PATENT DOCUMENTS

| 5,190,661 A | 3/1993 | Bruening et al. ............ 210/670 |
| 5,500,153 A | 3/1996 | Figueroa et al. ............ 252/548 |
| 5,652,206 A | 7/1997 | Bacon et al. ................ 510/101 |
| 5,686,014 A | 11/1997 | Baillely et al. ........ 252/186.33 |
| 6,218,350 B1 * | 4/2001 | Beggs et al. ................ 510/305 |
| 6,277,806 B1 * | 8/2001 | Berry et al. ................ 510/392 |

FOREIGN PATENT DOCUMENTS

| DE | 195 36 714 | 4/1997 |
| DE | 196 21 224 | 11/1997 |
| EP | 0 385 529 | 9/1990 |

(List continued on next page.)

OTHER PUBLICATIONS

PCT International Search Report in a PCT application PCT/EP 00/12532 Aug. 12, 2000.
Co–pending application: Davis et al.; Ser. No. 09/742,690; Filed—Dec. 20, 2000.

(List continued on next page.)

Primary Examiner—Yogendra N. Gupta
Assistant Examiner—Preeti Kumar
(74) Attorney, Agent, or Firm—Rimma Mitelman

(57) ABSTRACT

There is provided a method of delivering a benefit agent whereby a benefit agent is first loaded to a surface and subsequently unloaded and transferred and delivered to a second surface. More in particular, the benefit agent is first loaded onto a garment during a laundering process, and subsequently delivered to another surface. The benefit agents can be fragrance agents, perfumes, colour enhancers, fabric softening agents, polymeric lubricants, photoprotective agents, latexes, resins, dye fixative agents, encapsulated materials, antioxidants, insecticides, soil repelling agents, soil release agents, and cellulose fibers.

24 Claims, 12 Drawing Sheets

Figure 2:
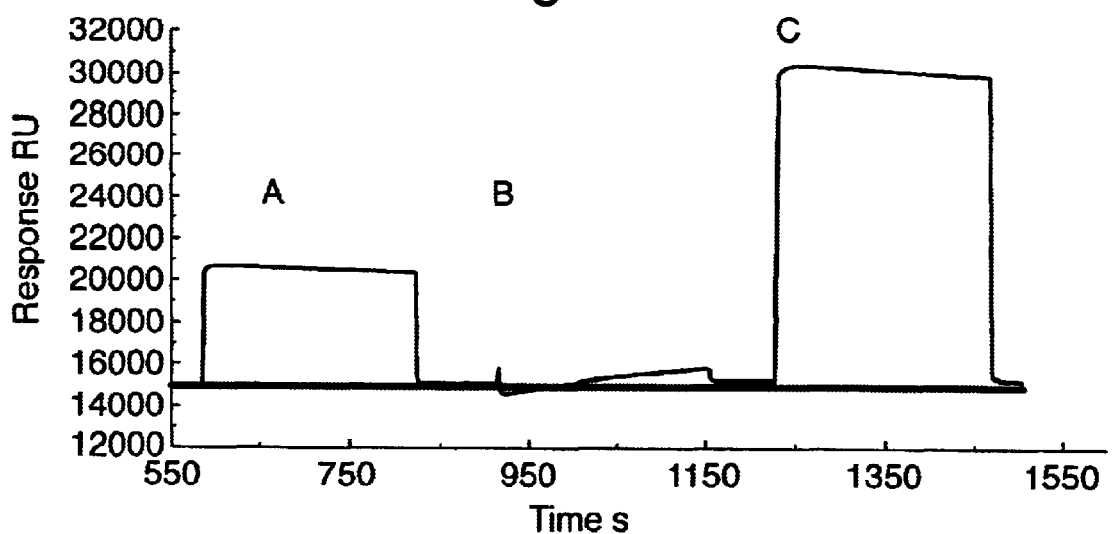

Event 2 - binding to second surface and unloading of benefit agent.

Event 1 - binding to surface 1

A — Non-specific/specific interaction
B — Dual specific interaction
C — Dual non-specific interaction

FOREIGN PATENT DOCUMENTS

| | | | |
|---|---|---|---|
| GB | WO 98/00500 | * | 8/1998 |
| WO | 94/25591 | | 11/1994 |
| WO | 95/02675 | | 1/1995 |
| WO | 95/09909 | | 4/1995 |
| WO | 98/00500 | | 1/1998 |
| WO | 98/01523 | | 1/1998 |
| WO | 98/06812 | | 2/1998 |
| WO | 98/07820 | | 2/1998 |
| WO | 98/23716 | | 6/1998 |
| WO | 98/56885 | | 12/1998 |
| WO | 99/02693 | | 1/1999 |
| WO | 99/12624 | | 3/1999 |
| WO | 99/23221 | | 5/1999 |
| WO | 99/36469 | | 7/1999 |
| WO | 99/57154 | | 11/1999 |
| WO | 99/57155 | | 11/1999 |
| WO | 99/57250 | | 11/1999 |
| WO | WO 99/57250 | * | 11/1999 |
| WO | 00/18864 | | 4/2000 |
| WO | WO 00/18864 | * | 4/2000 |
| WO | 00/36094 | | 6/2000 |
| WO | 01/07555 | | 2/2001 |
| WO | 01/1669 | | 3/2001 |

OTHER PUBLICATIONS

Co–pending application: Howell et al.; Ser. No. 09/742,693; Filed—Dec. 20, 2000.

Co–pending application: Hemingtonl et al.; Ser. No. 09/472,694; Filed—Dec. 20, 2000.

Co–pending application; Antheunisse et al.; Ser. No. 09/742,692; Filed—Dec. 20, 2000.

Co–pending application; Berry et al.; Ser. No. 09/712,561; Filed—Nov. 14, 2000.

Derwent Abstract of DE 196 21 224. May 25, 1996.

PCT International Search Report in a PCT application PCT/EP 00/12529. Aug. 12, 2000.

PCT International Search Report in a PCT application PCT/EP 00/12531. Aug. 12, 2000.

PCT International Search Report in a PCT application PCT/EP 00/12523. Aug. 12, 2000.

Derwent Abstract of JP 10 174583—Jun. 30, 1998.

PCT International Search Report in a PCT application PCT/EP 00/12530. Aug. 12, 2000.

* cited by examiner

Fig.1.
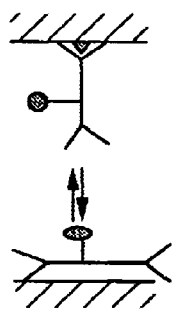 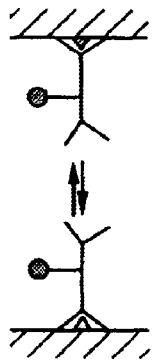 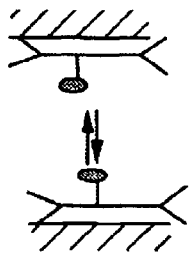
Event 2 - binding to second surface and unloading of benefit agent.
Event 1 - binding to surface 1
A
Non-specific/ specific interaction
B
Dual specific interaction
C
Dual non-specific interaction

Fig.8.

CAGGTGCAGCTGCAGCAGTCTGGGGGAGGCTTGGTACAGCCTGGGGGGTCTCTAAGACTC
TCCTGTGAAGCCTCTGGGCCTATCTTCAGTAGCAGAGCGATGTCCTGGTATCGCCAGGGT
CCAGGGAAGCAGCGCGAGCCGGTCGCATTTATTTCTACTGGTGGTGATACAAACTATGCT
AACTCCGTGAAGGGCCGATTCACCATCTCCAGAGACAACGCCAAGAACACGGTAGATCTG
CAAATGAACAATTTAAAACCTGAGGACACGGCCGTCTATTACTGTAAGACAATAGTCGAA
AAGGACTACTGGGGCCAGGGGACCCAGGTCACCGTCTCCTCAGGATCTCTCGAGCACCAT
CACCATCACCATGGATCCGATGCACACAAGAGTGAGGTTGCTCATCGGTTTAAAGATTTG
GGAGAAGAAATTTCAAAGCCTTGGTGTTGATTGCCTTTGCTCAGTATCTTCAGCAGTGT
CCATTTGAAGATCATGTAAAATTAGTGAATGAAGTAACTGAATTTGCAAAACATGTGTT
GCTGATGAGTCAGCTGAAAATTGTGACAAATCACTTCATACCCTTTTGGAGACAAATTA
TGCACAGTTGCAACTCTTCGTGAAACCTATGGTGAAATGGCTGACTGCTGTGCAAAACAA
GAACCTGGGAGAAATGAATGCTTCTTGCAACACAAAGATGACAACCCAAACCTCCCCCGA
TTGGTGAGACCAGAGGTTGATGTGATGTGCACTGCTTTTCATGACAATGAAGAGACATTT
TTGAAAAAATACTTATATGAAATTGCCAGAAGACATCCTTACTTTTATGCCCCGGAACTC
CTTTTCTTTGCTAAAAGGTATAAAGCTGCTTTTACAGAATGTTGCCAAGCTGCTGATAAA
GCTGCCTGCCTGTTGCCAAAGCTCGATGAACTTCGGGATGAAGGGAAGGCTTCGTCTGCC
AAACAGAGACTCAAGTGTGCCAGTCTCCAAAAATTTGGAGAAAGAGCTTTCAAAGCATGG
GCAGTAGCTCGCCTGAGCCAGAGATTTCCCAAAGCTGAGTTTGCAGAAGTTTCCAAGTTA
GTGACAGATCTTACCAAAGTCCACACGGAATGCTGCCATGGAGATCTGCTTGAATGTGCT
GATGACAGGGCGGACCTTGCCAAGTATATCTGTGAAAATCAAGATTCGATCTCCAGTAAA
CTGAAGGAATGCTGTGAAAAACCTCTGTTGGAAAAATCCCACTGCATTGCCGAAGTGGAA
AATGATGAGATGCCTGCTGACTTGCCTTCATTAGCTGCTGATTTTGTTGAAAGTAAGGAT
GTTTGCAAAAACTATGCTGAGGCAAAGGATGTCTTCTTGGGCATGTTTTTGTATGAATAT
GCAAGAAGGCATCCTGATTACTCTGTCGTGCTGCTGCTGAGACTTGCCAAGACATATGAA
ACCACTCTAGAGAAGTGCTGTGCCGCTGCAGATCCTCATGAATGCTATGCCAAAGTGTTC
GATGAATTTAAACCTCTTGTGGAAGAGCCTCAGAATTTAATCAAACAAAATTGTGAGCTT
TTTGAGCAGCTTGGAGAGTACAAATTCCAGAATGCGCTATTAGTTCGTTACACCAAGAAA
GTACCCCAAGTGTCAACTCCAACTCTTGTAGAGGTCTCAAGAAACCTAGGAAAAGTGGGC
AGCAAATGTTGTAAACATCCTGAAGCAAAAAGAATGCCCTGTGCAGAAGACTATCTATCC
GTGGTCCTGAACCAGTTATGTGTGTTGCATGAGAAAACGCCAGTAAGTGACAGAGTCACC
AAATGCTGCACAGAATCCTTGGTGAACAGGCGACCATGCTTTTCAGCTCTGGAAGTCGAT
GAAACATACGTTCCCAAAGAGTTTAATGCTGAAACATTCACCTTCCATGCAGATATATGC
ACACTTTCTGAGAAGGAGAGACAAATCAAGAAACAAACTGCACTTGTTGAGCTTGTGAAA

Fig.8(Cont.)

CACAAGCCCAAGGCAACAAAAGAGCAACTGAAAGCTGTTATGGATGATTTCGCAGCTTTT
GTAGAGAAGTGCTGCAAGGCTGACGATAAGGAGACCTGCTTTGCCGAGGAGGGTAAAAAA
CTTGTTGCTGCAAGTCAAGCTGCCTTAGGCTTAGGGGCCCAGCCGGCCATGGCCCAGGTG
CAGCTGCAGCAGTCTGGGGGAGGCTTGGTACAGCCTGGGGGGTCTCTAAGACTCTCCTGT
GAAGCCTCTGGGCCTATCTTCAGTAGCAGAGCGATGTCCTGGTATCGCCAGGGTCCAGGG
AAGCAGCGCGAGCCGGTCGCATTTATTTCTACTGGTGGTGATACAAACTATGCTAACTCC
GTGAAGGGCCGATTCACCATCTCCAGAGACAACGCCAAGAACACGGTAGATCTGCAAATG
AACAATTTAAAACCTGAGGACACGGCCGTCTATTACTGTAAGACAATAGTCGAAAAGGAC
TACTGGGGCCAGGGGACCCAGGTCACCGTCTCCTCAGGATCTCTCGAGCACCATCACCAT
CACCATGGATCCGGTAGCGGGAACTCCGGTAAGGGGTATCTGAAGTAATAA

Fig.9.

CAGGTGCAGCTGCAGGAGTCAGGGGGAGGATTGGTGCAGGCTGGGGGCTCTCTGAGACTC
TCCTGTGCAGCCTCGGGACGCGCCACCAGTGGTCATGGTCACTATGGTATGGGCTGGTTC
CGCCAGGTTCCAGGGAAGGAGCGTGAGTTTGTCGCAGCTATTAGGTGGAGTGGTAAAGAG
ACATGGTATAAAGACTCCGTGAAGGGCCGATTCACCATCTCCAGAGATAACGCCAAGACT
ACGGTTTATCTGCAAATGAACAGCCTGAAACCTGAAGATACGGCCGTTTATTATTGTGCC
GCTCGACCGGTCCGCGTGGATGATATTTCCCTGCCGGTTGGGTTTGACTACTGGGGCCAG
GGGACCCAGGTCACCGTCTCCTCACAGGTGCAGCTGCAGCAGTCTGGGGGAGGCTTGGTA
CAGCCTGGGGGGTCTCTAAGACTCTCCTGTGAAGCCTCTGGGTTCATCTTCAGTAGCAGA
GCGATGTCCTGGTATCGCCAGGGTCCAGGGAAGCAGCGCGAGCCGGTCGCATTTATTTCT
ACTGGTGGTGATACAAACTATGCTAACTCCGTGAAGGGCCGATTCACCATCTCCAGAGAC
AACGCCAAGAACACGGTAGATCTGCAAATGAACAATTTAAAACCTGAGGACACGGCCGTC
TATTACTGTAAGACAATAGTCGAAAAGGACTACTGGGGCCAGGGGAACCAGGTCACCGTC
TCCTCAGGATCTCATCACCATCACCATCACGGATCCACCTCCATTGAAGGTCGTACCCAG
TCTCACTACGGTCAGTGTGGTGGTATTGGTTACTCCGGTCCAACCGTCTGTGCCTCTGGT
ACCACCTGTCAGGTTCTGAACCCTTACTACTCCCAGTGTCTGTAATAA

Fig. 10.

Binding Activity Of Anti-RR6-VHH8-CBD P.Pastoris Supernatants

- RR6-BSA
- Keratin
- PBS
- Ethylcellulose
- Filter

Fig. 11.
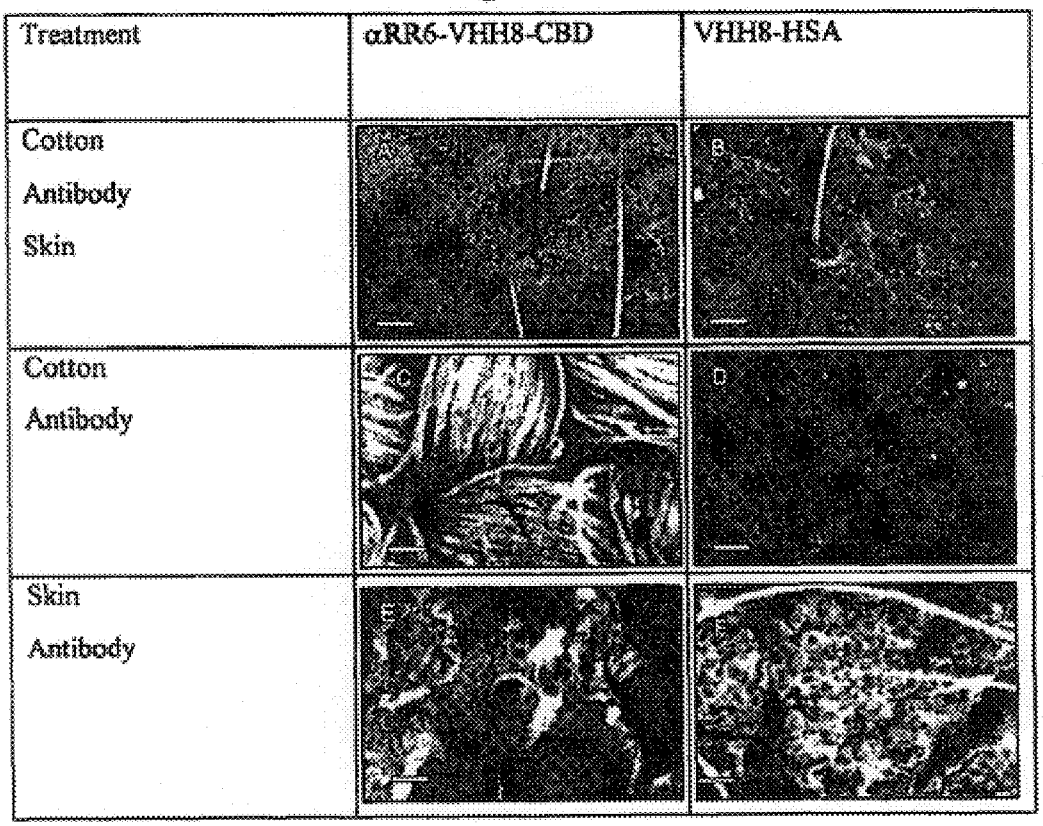
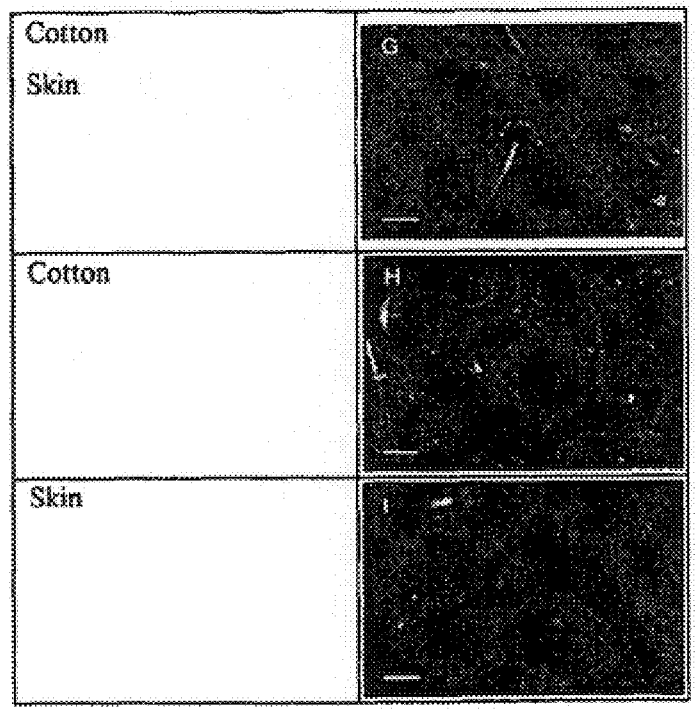
—100μ

Fig. 12.

| Treatment | Skin Image | Cotton Image |
|---|---|---|
| Cotton<br>Antibody<br>Oil body RR6/nile red<br>Skin |  |  |
| Cotton<br>Oil body nile red/RR6<br>Skin |  | 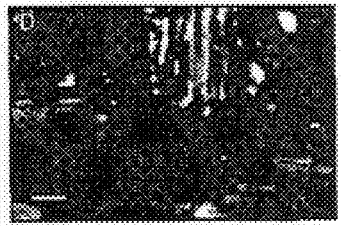 |
| Cotton<br>Antibody<br>Oil body nile red<br>Skin |  | 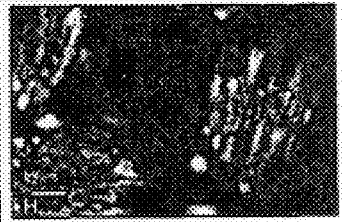 |
| Cotton<br>Oil body nile red<br>Skin |  |  |
| I: Skin & antibody & oil body RR6/nile red<br>OR<br>J: Cotton & antibody & oil body RR6/nile red | 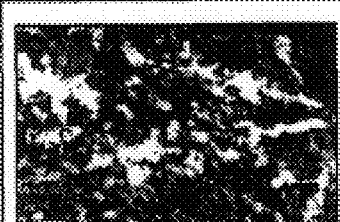 |  |
| K: Skin & antibody & oil body nile red<br>OR<br>L: Cotton and antibody & oil body nile red |  | 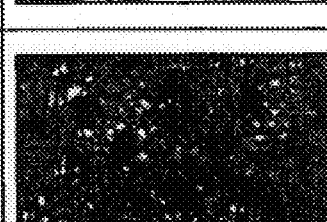 |

100μ

| Treatment | Skin | Cotton |
|---|---|---|
| Anti-RR6-VHH8-CBD<br>Oil bodies RR6/nile red | A | B |
| Anti-RR6-CBD<br>Oil bodies RR6/nile red | C | D |
| Oil bodies RR6/nile red | E | F |
| Anti-RR6-VHH8-CBD | G | H |
| Anti-RR6-CBD | I | J |

— 100μ

— 100μ

METHOD OF DELIVERING A BENEFIT AGENT

FIELD OF THE INVENTION

The present invention relates to a method of delivering a benefit agent to a surface. More in particular, it relates to a method whereby a benefit agent is loaded to a first surface and subsequently unloaded and transferred and delivered to a second surface. In a preferred embodiment, it relates to the transfer of benefit agent, loaded on to a garment during the washing process, and subsequent delivery of the benefit agent to another surface.

BACKGROUND

Conventionally, benefit agents, such as bleach and perfume, are incorporated in detergent compositions, adsorbed onto surfaces, and act on the garments during the washing process. After the washing process, the effects are generally short-lived. In addition, large quantities of benefit have to be present to achieve an effect.

WO-A-98/56885 (Unilever) discloses a bleaching enzyme which is capable of generating a bleaching chemical and having a high binding affinity for stains present on fabrics, as well as an enzymatic bleaching composition comprising said bleaching enzyme, and a process for bleaching stains on fabrics. The binding affinity may be formed by a part of the polypeptide chain of the bleaching enzyme, or the enzyme may comprise an enzyme part which is capable of generating a bleach chemical that is coupled to a reagent having the high binding affinity for stains present on fabrics. In the latter case the reagent may be bispecific, comprising one specificity for stain and one for enzyme. Examples of such bispecific reagents mentioned in the disclosure are antibodies, especially those derived from Camelidae having only a variable region of the heavy chain polypeptide ($V_{HH}$), peptides, peptidomimics, and other organic molecules. The enzyme which is covalently bound to one functional site of the antibody usually is an oxidase, such as glucose oxidase, galactose oxidase and alcohol oxidase, which is capable of forming hydrogen peroxide or another bleaching agent. Thus, if the multi-specific reagent is an antibody, the enzyme forms an enzyme/antibody conjugate which constitutes one ingredient of a detergent composition. During washing, said enzyme/antibody conjugate of the detergent composition is targeted to stains on the clothes by another functional site of the antibody, while the conjugated enzyme catalyzes the formation of a bleaching agent in the proximity of the stain and the stain will be subjected to bleaching.

WO-A-98/00500 (Unilever) discloses detergent compositions wherein a benefit agent is delivered onto fabric by means of peptide or protein deposition aid having a high affinity for fabric. The benefit agent can be a fabric softening agent, perfume, polymeric lubricant, photosensitive agent, latex, resin, dye fixative agent, encapsulated material, antioxidant, insecticide, soil repelling agent, or a soil release agent. The benefit agent is attached or adsorbed to a peptide or protein deposition aid having a high affinity to fabric. Preferably, the deposition aid is a fusion protein containing the cellulose binding domain of a cellulase enzyme. The compositions are said to effectively deposit the benefit agent onto the fabric during the laundering process.

According to DE-A-196 21 224 (Henkel), the transfer of textile dyes from one garment to another during a washing or rinsing process may be inhibited by adding antibodies against the textile dye to the wash or rinse liquid.

WO-A-98/07820 (P&G) discloses amongst others rinse treatment compositions containing antibodies directed at cellulase and standard softener actives (such as DEQA). WO 99/27368 describes the use of a displaceable moiety able to bind to 2 different surfaces. However, all interactions are specific (to an analyte of interest and a mimitope) and the assay is specifically aimed at measuring an analyte of interest for a Unipath application.

There is a need for extending the length of time that a benefit acts on the garment after the washing process. There is also a need to transfer the benefit agent from the garment onto another surface, for example during wearing or storage of the garment, thereby extending the scope of benefit that can be delivered and achieved.

Surprisingly, it has now been found that antibodies can bind to one surface through non-specific charge interaction and then unload on to a second surface through specific e.g. antigen/antibody interactions. Opportunities for other non-specific interactions include e.g. charge, hydrophobicity/hydrophilicity, trapping due to size constraints.

DETAILED DESCRIPTION OF THE INVENTION

According to the invention, a benefit agent is first loaded to a surface and subsequently unloaded and transferred and delivered to a second surface. The benefit agent is chosen to impart a benefit onto the surface, which may be a garment, skin, or a ligand thereof. For skin applications, this benefit agent can be bleach, moisturisers, skin softeners (e.g. silicones), emollients, sunscreens, lipids, vitamins, anti-microbial agents, anti-aging benefits, anti-perspirants, skin lightening agents, fabripseuticals, skin-sensory cues (such as menthol, capsasin, silicones) and chemicals. For laundry, the benefit agent can be in the form of a bleaching agent (produced by, for example, bleaching enzymes) that can de-colourise stains, fragrances, colour enhancers, fabric regenerators, softening agents, finishing agents/protective agents, and the like. These will be described in more detail below. The benefit agent may be encapsulated in sensitised particles, bound directly to reagent as a fusion construct, or bound to antibody as a bi-head (WO-A-99/23221). The term antibody includes monoclonal and antibody fragments (scFv, Fab, Fv, VHH, camelised VH).

The benefit agent is loaded onto the first surface by means of a carrying agent. The reagents carrying the benefit agent can bind specifically or non-specifically to surfaces and then bind to a second surface via specific or non-specific interactions. The possible scenarios are depicted in FIG. 1, which shows the binding of the carrying agent/benefit agent through non-specific interaction (A, C) to the first surface and the subsequent unloading of carrying agent/benefit agent through non-specific (C) or specific (A) interactions with a second surface.

Where specific interactions are involved for binding to both surfaces, then displacement to the second surface may result from the reagent having an increased affinity for the second surface over the first. The unloading of the benefit agent may result from pH changes, pressure/abrasion, affinity of the benefit being greater for the second surface than the reagent. Surfaces can be loaded with benefit agent through protein, antibody, peptide, DNA or carbohydrate interactions.

For laundry applications, the primary surface to be loaded with antibody is the fabric. Specifically for laundry applications, the reagent may be loaded all over the garment or be targeted to a specific site, e.g. a site of damage or the underarm region.

As used herein, the term "multi-specific binding molecule" means a molecule which at least can associate onto fabric and also capture benefit agent. Similarly, the term "bi-specific binding molecule" as used herein indicates a molecule which can associate onto fabric and capture benefit agent.

In the first step the binding molecule carrying the benefit agent is directly delivered to the fabric, for example a garment, preferably at relatively high concentration, thus enabling the loading of the benefit agent to the fabric in an efficient way.

Examples of the second surface for the subsequent loading include skin, microbes, lipids, steroids, fabric, ligand thereof. For non-laundry applications, the surfaces can be plastic, metal, polystyrene (exemplified in Example 3), hair (whereby the second surface could be a yeast causing dandruff), or a cleaning cloth whereby the second surface is a microbe. Another way of carrying out the invention is to use binding molecules to remove unwanted components from the first surface, e.g. soil or microbes.

In a second step, the carrying agent is contacted with the benefit agent, which may be contained in a dispersion or solution, preferably an aqueous solution, or in a dry environment, e.g. tranfer to skin from garment whilst in wear, thus enabling the benefit agent to bind to the binding molecule through another specificity of said binding molecule.

The multi-specific binding molecule can be any suitable molecule with at least two functionalities, i.e. having a high binding affinity to the fabric to be treated and being able to bind to a benefit agent, thereby not interfering with the pre-determined activity of the benefit agent and possible other activities aimed. In a preferred embodiment, said binding molecule is an antibody, or an antibody fragment, or a derivative thereof. The present invention can be advantageously used in, for example, treating stains on fabrics, preferably by bleaching said stains. In a first step, the binding molecule is applied, preferably on the stain. The benefit agent which is then bound to the binding molecule preferably is an enzyme or enzyme part, more preferably an enzyme or enzyme capable of catalyzing the formation of a bleaching agent under conditions of use. The enzyme or enzyme part is usually contacted to the binding molecule (and the stains) by soaking the pre-treated fabric into a dispersion or solution comprising the enzyme or enzyme part. The dispersion or solution which usually but not necessarily is an aqeous dispersion or solution also comprises ingredients generating the bleaching agent, or such ingredients are added later. Preferably, the enzyme or enzyme part and said other ingredients generating a bleach are contained in a washing composition, and the step of binding the enzyme (or part thereof) to the binding molecule and generating the bleaching agent is performed during the wash. Alternatively, the benefit agent may be added prior to or after washing, for example in the rinse or prior to ironing.

The targeting of the benefit agent according to the invention which in this typical example is a bleaching enzyme, results in a higher concentration of bleaching agent in the proximity of the stains to be treated, before, during or after the wash. Alternatively, less bleaching enzyme is needed as compared to known non-targeting or less efficient targeting methods of treating stains.

Another typical and preferred example of the use of the present invention is to direct a fragrance (such as a perfume) to fabric and to a second surface, e.g. skin, so that it is released over time. A further typical use of the present invention is treating a surface, e.g. fabric where the colour is faded by directing a benefit agent to the area in order to colour that region. Similarly, a damaged area of a fabric can be (pre-)treated to direct a repair of cellulose fibers which are bound by the antibodies to this area. These agents are for example suitably added to the pre-treated fabric after washing, in the rinse.

Other applications, such as using fabric softening agents, polymeric lubricants, photoprotectove agents, latexes, resins, dye fixative agents, encapsulated materials antioxidants, insexticides, soil repelling agents or soil release agents, as well as other agents of choice, and ways and time of adding the agents to the pre-treated fabric are fully within the ordinary skill of a person skilled in the art.

In order to be more fully understood, certain elements of the present invention will be described hereinafter in more detail. Reference is also made to WO 98/56885, referred to above, the content of which is incorporated herewith by reference.

1.0 Binding Molecules

In the first step according to the invention a multi-specific binding molecule is delivered to fabric, said binding molecule having a high affinity to said area through one specificity.

The degree of binding of a compound A to another molecule B can be generally expressed by the chemical equilibrium constant $K_d$ resulting from the following reaction:

$$[A] + [B] \Leftrightarrow [A \equiv B]$$

The chemical equilibrium constant $K_d$ is then given by:

$$K_d = \frac{[A] \times [B]}{[A \equiv B]}$$

Whether the binding of a molecule to the fabric is specific or not can be judged from the difference between the binding ($K_d$ value) of the molecule to one type of fabric, versus the binding to another type of fabric material. For applications in laundry, said material will be a fabric such as cotton, polyester, cotton/polyester, or wool. However, it will usually be more convenient to measure $K_d$ values and differences in $K_d$ values on other materials such as a polystyrene microtitre plate or a specialised surface in an analytical biosensor. The difference between the two binding constants should be minimally 10, preferably more than 100, and more preferably, more that 1000. Typically, the molecule should bind to the fabric, or the stained material, with a $K_d$ lower than $10^{-4}$ M, preferably lower than $10^{-6}$ M and could be $10^{-10}$ M or even less. Higher binding affinities ($K_d$ of less than $10^{-5}$ M) and/or a larger difference between the one type of fabric and another type (or background binding) would increase the deposition of the benefit agent. Also, the weight efficiency of the molecule in the total composition would be increased and smaller amounts of the molecule would be required.

Several classes of binding molecules can be envisaged which deliver the capability of specific binding to fabrics, to which one would like to deliver the benefit agent. In the following we will give a number of examples of such molecules having such capabilities, without pretending to be exhaustive. Reference is also made in this connection to WO-A-98/56885 (Unilever), the disclosure of which is incorporated herein by reference.

1.1 Antibodies

Antibodies are well known examples of compounds which are capable of binding specifically to compounds against which they were raised. Antibodies can be derived from several sources. From mice, monoclonal antibodies can be obtained which possess very high binding affinities. From such antibodies, Fab, Fv or scFv fragments, can be prepared which have retained their binding properties. Such antibodies or fragments can be produced through recombinant DNA technology by microbial fermentation. Well known production hosts for antibodies and their fragments are yeast, moulds or bacteria.

A class of antibodies of particular interest is formed by the Heavy Chain antibodies as found in Camelidae, like the camel or the llama. The binding domains of these antibodies consist of a single polypeptide fragment, namely the variable region of the heavy chain polypeptide ($V_{HH}$). In contrast, in the classic antibodies (murine, human, etc.), the binding domain consist of two polypeptide chains (the variable regions of the heavy chain ($V_H$) and the light chain ($V_L$)). Procedures to obtain heavy chain immunoglobulins from Camelidae, or (functionalized) fragments thereof, have been described in WO 94/04678 (Casterman and Hamers) and WO 94/25591 (Unilever and Free University of Brussels).

Alternatively, binding domains can be obtained from the $V_H$ fragments of classical antibodies by a procedure termed "camelization". Hereby the classical $V_H$ fragment is transformed, by substitution of a number of amino acids, into a $V_{HH}$-like fragment, whereby its binding properties are retained. This procedure has been described by Riechmann et al. in a number of publications (J. Mol. Biol. (1996) 259, 957–969; Protein. Eng. (1996) 9, 531–537, Bio/Technology (1995) 13, 475–479). Also $V_{HH}$ fragments can be produced through recombinant DNA technology in a number of microbial hosts (bacterial, yeast, mould), as described in WO-A-94/29457 (Unilever).

Methods for producing fusion proteins that comprise an enzyme and an antibody or that comprise an enzyme and an antibody fragment are already known in the art. One approach is described by Neuberger and Rabbits (EP-A-0 194 276). A method for producing a fusion protein comprising an enzyme and an antibody fragment that was derived from an antibody originating in Camelidae is described in WO-A-94/25591. A method for producing bispecific antibody fragments is described by Holliger et al. (1993) PNAS 90, 6444–6448.

WO-A-99/23221 (Unilever) discloses multivalent and multispecific antigen binding proteins as well as methods for their production, comprising a polypeptide having in series two or more single domain binding units which are preferably variable domains of a heavy chain derived from an immunoglobulin naturally devoid of light chains, in particular those derived from a Camelid immunoglobulin.

An alternative approach to using fusion proteins is to use chemical cross-linking of residues in one protein for covalent attachment to the second protein using conventional coupling chemistries, for example as described in Bioconjugate Techniques, G. T. Hermanson, ed. Academic Press, Inc. San Diego, Calif., USA. Amino acid residues incorporating sulphydryl groups, such as cysteine, may be covalently attached using a bispecific reagent such as succinimidyl-maleimidophenylbutyrate (SMPB), for example. Alternatively, lysine groups located at the protein surface may be coupled to activated carboxyl groups on the second protein by conventional carbodiimide coupling using 1-ethyl-3-[3-dimethylaminopropyl] carbodiimide (EDC) and N-hydroxysuccinimide (NHS).

A particularly attractive feature of antibody binding behaviour is their reported ability to bind to a "family" of structurally-related molecules. For example, in Gani et al. (J. Steroid Biochem. Molec. Biol. 48, 277–282) an antibody is described that was raised against progesterone but also binds to the structurally-related steroids, pregnanedione, pregnanolone and 6-hydroxy-progesterone. Therefore, using the same approach, antibodies could be isolated that bind to a whole "family" of stain chromophores (such as the polyphenols, porphyrins, or caretenoids as described below). A broad action antibody such as this could be used to treat several different stains when coupled to a bleaching enzyme.

1.2 Fusion Proteins Comprising a Cellulose Binding Domain (CBD)

Another class of suitable and preferred binding molecules for the purpose of the present invention are fusion proteins comprising a cellulose binding domain and a domain having a high binding affinity for another ligand. The cellulose binding domain is part of most cellulase enzymes and can be obtained therefrom. CBDs are also obtainable from xylanase and other hemicellulase degrading enzymes. Preferably, the cellulose binding domain is obtainable from a fungal enzyme origin such as Humicola, Trichoderma, Thermonospora, Phanerochaete, and Aspergillus, or from a bacterial origin such as Bacillus, Clostridium, Streptomyces, Cellulomonas and Pseudomonas. Especially preferred is the cellulose binding domain obtainable from *Trichoderma reesei*.

In the fusion protein according to the invention, the cellulose binding domain is fused to a second domain having a high binding affinity for another ligand. Preferably, the cellulose binding domain is connected to the domain having a high binding affinity for another ligand by means of a linker consisting of about 0–20, preferably about 2–15, more preferably of 2–5 amino acids.

The second domain having a high binding affinity to another ligand may, for example, be an antibody or an antibody fragment. Especially preferred are heavy chain antibodies such as found in Camelidae.

The CBD antibody fusion binds to the fabric via the CBD region, thereby allowing the antibody domain to bind to corresponding antigens that comprise or form part of the benefit agent.

The fusion protein may comprise more than one cellulose binding domain and an antibody fragment or derivative thereof, or coversely one cellulose binding domain fused to more than one antibody in that the antibody may have the same or different specificities.

1.3 Peptides

Peptides usually have lower binding affinities to the substances of interest than antibodies. Nevertheless, the binding properties of carefully selected or designed peptides can be sufficient to provide the desired selectivity to bind a benefit agent or to be used in an aimed process, for example an oxidation process.

A peptide which is capable of binding selectively to a substance which one would like to oxidise, can for instance be obtained from a protein which is known to bind to that specific substance. An example of such a peptide would be a binding region extracted from an antibody raised against that substance. Other examples are proline-rich peptides that are known to bind to the polyphenols in wine.

Alternatively, peptides which bind to such substances can be obtained by the use of peptide combinatorial libraries. Such a library may contain up to $10^{10}$ peptides, from which the peptide with the desired binding properties can be isolated. (R. A. Houghten, Trends in Genetics, Vol 9, no &, 235–239). Several embodiments have been described for this procedure (J. Scott et al., Science (1990) 249, 386–390; Fodor et al., Science (1991) 251, 767–773; K. Lam et al., Nature (1991) 354, 82–84; R. A. Houghten et al., Nature (1991) 354, 84–86).

Suitable peptides can be produced by organic synthesis, using for example the Merrifield procedure (Merrifield (1963) J.Am.Chem.Soc. 85, 2149–2154). Alternatively, the peptides can be produced by recombinant DNA technology in microbial hosts (yeast, moulds, bacteria) (K. N. Faber et al. (1996) Appl. Microbiol. Biotechnol. 45, 72–79).

1.4 Peptidomimics

In order to improve the stability and/or binding properties of a peptide, the molecule can be modified by the incorporation of non-natural amino acids and/or non-natural chemical linkages between the amino acids. Such molecules are called peptidomimics (H. U. Saragovi et al. (1991) Bio/Technology 10, 773–778; S. Chen et al. (1992) Proc.Natl.Acad. Sci. USA 89, 5872–5876). The production of such compounds is restricted to chemical synthesis.

1.5 Other Organic Molecules

The list on proteins and peptides described so far are by no means exhaustive. Other proteins, for example those described in WO-A-00/40968, which is incorporated herein by reference, can also be used.

It can be readily envisaged that other molecular structures which need not be related to proteins, peptides or derivatives thereof, can be found which bind selectively to substances one would like to oxidise with the desired binding properties. For example, certain polymeric RNA molecules which have been shown to bind small synthetic dye molecules (A. Ellington et al. (1990) Nature 346, 818–822). Such binding compounds can be obtained by the combinatorial approach, as described for peptides (L. B. McGown et al. (1995), Analytical Chemistry, 663A-668A).

This approach can also be applied for purely organic compounds which are not polymeric. Combinatorial procedures for synthesis and selection for the desired binding properties have been described for such compounds (Weber et al. (1995) Angew. Chem. Int. Ed. Engl. 34, 2280–2282; G. Lowe (1995), Chemical Society Reviews 24, 309–317; L. A. Thompson et al. (1996) Chem. Rev. 96, 550–600). Once suitable binding compounds have been identified, they can be produced on a larger scale by means of organic synthesis.

2.1 Bleaching Enzymes

As mentioned above, the benefit agent can be bleach, moisturisers, skin softeners (e.g. silicones), emollients, sunscreens, lipids, vitamins, anti-microbial agents, anti-aging benefits, anti-perspirants, skin lightening agents, fabripseuticals, and chemicals. Suitable bleaching enzymes which are useful for the purpose of the present invention are capable of generating a bleaching chemical.

The bleaching chemical may be hydrogen peroxide which is preferably enzymatically generated. The enzyme for generating the bleaching chemical or enzymatic hydrogen peroxide-generating system is generally selected from the various enzymatic hydrogen peroxide-generating systems which are known in the art. For example, one may use an amine oxidase and an amine, an amino acid oxidase and an amino acid, cholesterol oxidase and cholesterol, uric acid oxidase and uric acid, or a xanthine oxidase with xanthine. Alternatively, a combination of a $C_1$–$C_4$ alkanol oxidase and a $C_1$–$C_4$ alkanol is used, and especially preferred is the combination of methanol oxidase and ethanol. The methanol oxidase is preferably isolated from a catalase-negative *Hansenula polymorpha* strain. (see for example EP-A-244 920 of Unilever). The preferred oxidases are glucose oxidase, galactose oxidase and alcohol oxidase.

A hydrogen peroxide-generating enzyme could be used in combination with activators which generate peracetic acid. Such activators are well-known in the art. Examples include tetraacetylethylenediamine (TAED) and sodium nonanoyl-oxybenzenesulphonate (SNOBS). These and other related compounds are described in fuller detail by Grime and Clauss in Chemistry & Industry (Oct. 15, 1990) 647–653. Alternatively, a transition metal catalyst could be used in combination with a hydrogen peroxide generating enzyme to increase the bleaching power. Examples of manganese catalysts are described by Hage et al. (1994) Nature 369, 637–639.

Alternatively, the bleaching chemical is hypohalite and the enzyme is then a haloperoxidase. Preferred haloperoxidases are chloroperoxidases and the corresponding bleaching chemical is hypochlorite. Especially preferred chloroperoxidases are vanadium chloroperoxidases, for example from *Curvularia inaequalis*.

Alternatively, peroxidases or laccases may be used. The bleaching molecule may be derived from an enhancer molecule that has reacted with the enzyme. Examples of laccase/enhancer systems are given in WO-A-95/01426. Examples of peroxidase/enhancer systems are given in WO-A-97/11217.

Suitable examples of bleaches include also photobleaches. Examples of photobleaches are given in EP-A-379 312 (British Petroleum), which discloses a water-insoluble photobleach derived from anionically substituted porphine, and in EP-A-035 470 (Ciba Geigy), which discloses a textile treatment composition comprising a photobleaching component.

2.2 Fragrances

The benefit agent can be a fragrance (perfume), thus through the application of the invention it is able to impart onto the fabric and second surface a fragrance that will remain associated with the surfaces for a longer period of time than conventional methods. Fragrances can be captured by the binding molecule directly, more preferable is the capture of "packages" or vesicles containing fragrances. The fragrances or perfumes may be encapsulated, e.g. in latex microcapsules.

2.3 Colour Enhancers

The benefit agent can be an agent used to replenish colour on garments. These can be dye molecules or, more preferable, dye molecules incorporated into "packages" or vesicles enabling larger deposits of colour.

2.4 Fabric Regenerating Agents

The benefit agent can be an agent able to regenerate damaged fabric. For example, enzymes able to synthesize cellulose fibres could be used to build and repair damaged fibres on the garment.

2.5 Others

A host of other agents could be envisaged to impart a benefit to the second surface, e.g. fabric or skin. These will be apparant to those skilled in the art and will depend on the benefit being captured at the fabric surface. Examples of softening agents are clays, cationic surfactants or silicon compounds. Examples of finishing agents/protective agents are polymeric lubricants, soil repelling agents, soil release agents, photo-protective agents (sunscreens), anti-static agents, dye-fixing agents, anti-bacterial agents and anti-fungal agents.

3.1 The Surfaces

For laundry detergent applications, several classes of natural or man-made fabrics can be envisaged, in particular cotton. Such macromolecular compounds have the advantage that they can have a more immunogenic nature, i.e. that it is easier to raise antibodies against them. Furthermore, they are more accessible at the surface of the fabric than for instance coloured substances in stains, which generally have a low molecular weight.

An important embodiment of the invention is to use a binding molecule (as described above) that binds to several different types of fabrics. This would have the advantage of enabling a single benefit agent to be deposited to several different types of fabric.

The skin's natural substrates could be used to activate the benefit agent once it comes into contact with the skin.

The invention will now be further illustrated by the following, non-limiting examples.

EXAMPLE 1

Loading of a Cotton Surface with a Reagent via Non-specific Charge Interaction. This example relates to the isolation of llama VHH antibodies that bind to red wine stained cotton through non-specific interactions.

1.1 VHH Antibody Semi-Synthetic Antibody Library

Antibody fragments that bind specifically to antigen can be derived from synthetic antibody libraries (Marks, J., Hoogenboom, H., Bonnert, T., McCafferty, J., Griffiths, A., Winter, G., 1991. By-passing immunization. Human antibody from V-gene libraries displayed on phage. J.Mol.Biol.222, 581–597).

A semi-synthetic library of llama heavy-chain variable domain (VHH) genes was constructed as previously described (Synthetic Library—Llama Fragments Application no. EP 9930 0351). The library was stored at −70° C. as phage stocks.

1.2 Panning of the Library

Red wine binding phage were selected by panning against polystyrene tubes sensitised with red wine (Co-op Cote du Rhone) or cotton strands stained with the red wine in the presence of phosphate buffered saline (PBS) with 0.15% Tween (PBST) (as the surfactant) pH 7.2. All surfaces were pre-blocked for 30 minutes with 2%BSA/1% marvel (blocking agent) in PBS. Approximately $10^9$ phage displaying antibody fragments were added to each panning surface in a total volume of 1 ml blocking agent in PBST and allowed to bind to the surfaces for 3 hours. Unbound phage was removed by washing 20× with PBST followed by 20× with PBS. Bound phage were eluted by incubating the panning surfaces with 1 ml 0.2M glycine pH2.2 with 10 mg/ml BSA. Eluates were removed to another tube and neutralised with 30 µl 2M Tris. E. coli TG1 strain were re-infected with the eluted phage and grown overnight.

Phage were rescued from the overnight cultures and PEG precipitated using standard methods. The process was repeated a further 2 times to enrich the library for red wine binders.

1.3 Production of Soluble Antibody Fragments that Bind to Red Wine

After 3 rounds of panning, individual colonies were grown in 150 µl 2TY (1.6% bacto-tryptone, 1% yeast extract, and 1% NaCl) containing 100 µg/ml ampicillin and 1% glucose (2TY amp/glucose), in a well of a microtitre plate. When the media was turbid, 130 µl was transferred to a well of a V-bottom plate, and the cells pelleted by centrifugation. Soluble antibody fragments with myc tails, for detection purposes, were induced by resuspending the cells in 150 µl 2TY/amp containing 1 mM IPTG, and incubating overnight at 25° C. Cells were pelleted and supernatant assayed.

1.4 Solid-Phase Binding ELISA

Binding activity of VHH to red wine was shown via ELISA.

High-binding Greiner microtitre plates were sensitised with 100 µl/well red wine or PBS only for about 60 hours at 37° C. Plates were washed with PBST and then blocked with 200 µl/well 1% BSA/PBST for 1 hour at 37° C. 50 µl crude E. coli supernatant, for each colony, containing VHHs was premixed with 50 µl PBST and added to the appropriate wells of the blocked plates. VHHs were allowed to bind to the sensitised surfaces for 1½ hours at 37° C. Unbound fragments were removed by washing 4× with PBST. 100 µl/well of an appropriate dilution of mouse anti-myc antibody (in house) in PBST was added and incubated for 1 hour at 37° C. Plates were washed as previously and 100 µl/well of an appropriate dilution of alkaline phosphatase conjugated goat anti-mouse (Jackson) in PBST added and incubated as before. Plates were again washed and alkaline phosphatase activity was detected by adding 100 µl/well substrate solution: 1 mg/ml pNPP in 1M diethanolamine/1 mM $MgCl_2$. When the colour had developed an absorbance reading at 405 nm was taken: the greater the optical density, the greater the level of binding of the VHH to the sensitised surface.

Clones giving a positive signal to the red wine sensitised plate and no background signal to the PBS sensitised plate were selected and soluble VHHs produced on a 10 ml scale as previously described. Clones named 1, 3, and 6 were derived from the library panned against polystyrene sensitised tube. Clones 8, 10, and 11 were derived from the library panned against red wine stained cotton.

Binding to red wine sensitised plates was rechecked, in duplicate, by ELISA as previously described. Results are in Table 1. No binding was detected to the PBS sensitised plate. However, not all the clones selected for previously binding to red wine sensitised plate when produced in microtitre plates, still gave positive signals. This is not surprising given that production of antibody fragments on a very small scale and analysis of the supernatant can be an unreliable process.

In addition to the solid plate ELISA, binding of the fragments to red wine stained cotton over that of unstained white cotton was assessed using an ELISA format. 0.5 cm diameter discs of white cotton or red wine stained cotton were placed in a well of a 0.45µ nylon filter microtitre plate (Millipore) and prewashed in PBST for 15 minutes at room temperature. 50 µl crude E. coli supernatant together with equal volume of 0.05% Tween in PBS pH7 was added to each disc type in duplicate and incubated for 1½ hour at room temperature with shaking. The filter plate was washed 9× with PBS 0.05% Tween and 1001 µl/well of an appropriate dilution of mouse anti-myc antibody added in PBST. Incubation was for 1 hour as previously. Plates were washed 9× as before and 100 µl/well of an alkaline phosphatase conjugated goat anti-mouse antibody (Jackson) added at an appropriate dilution in PBST. Incubation was as for the previous step. Plates were again washed and 100 µl/well pNPP/DEA substrate added. Colour was allowed to develop and then substrate was removed to a solid microtitre plate and absorbance read at 405 nm. Results are in Table 2. Unlike the solid plate ELISA all clones bound to the red wine sensitised surface (being cotton in this instance). However, the background signals to white cotton were very high. Clone 10 was the only VHH not to give a greater signal to the red wine stained cotton over that of the unstained white cotton. The level of binding to stained cotton did not correlate with the results obtained for the solid plate ELISA.

TABLE 1

| Clone Number | OD405 Red Wine | OD405 PBS | Mean OD405 Red Wine-PBS |
|---|---|---|---|
| 1 | 0.34 | 0 | 0.39 |
|   | 0.43 | 0 |   |
| 3 | 0.21 | 0 | 0.20 |
|   | 0.18 | 0 |   |
| 6 | 2.36 | 0 | 2.20 |
|   | 2.03 | 0 |   |
| 8 | 0 | 0 | 0.01 |
|   | 0.01 | 0 |   |
| 10 | 0 | 0 | 0 |
|   | 0 | 0 |   |
| 11 | 0.01 | 0 | 0.01 |
|   | 0 | 0 |   |

TABLE 2

| Clone Number | OD405 Red Wine Cotton | OD405 White Cotton | Mean OD405 Red Wine-White Cotton | PI |
|---|---|---|---|---|
| 1 | 1.78 | 0.70 | 1.33 | 9.8 |
|   | 2.12 | 0.54 |   |   |
| 3 | 0.99 | 0.36 | 0.55 | 9.6 |
|   | 0.80 | 0.32 |   |   |
| 6 | 1.98 | 0.26 | 1.53 | 10.3 |
|   | 1.98 | 0.64 |   |   |
| 8 | 0.64 | 0.21 | 0.44 | 9.4 |
|   | 0.66 | 0.20 |   |   |
| 10 | 0.66 | 0.41 | 0.04 | 8.9 |
|   | 0.68 | 0.44 |   |   |
| 11 | 0.75 | 0.17 | 0.57 | 9.7 |
|   | 0.73 | 0.17 |   |   |

Surprisingly, the amount of binding to red wine stained cotton over that of white cotton correlated with the deduced pI of the clones, i.e. the higher the pI the greater the specific signal to red wine stained cotton over background signal to white cotton.

EXAMPLE 2

Demonstration of Antibody Binding to one Surface and then Being Reloaded on to a Second Surface. This example relates to the initial binding of an antibody to a non-specific surface and subsequent unloading and binding to a second surface. This principle has been demonstrated using a non-specific surface and a specifically sensitised surface on a Biacore Biosensor (Biacore AB, Sweden). The reagents involved are human chorionic gonadotrophin (hcg) that is used to create the specific surface, and mouse monoclonal antibody 3468 which specifically binds hcg. 3468 was prepared using standard monoclonal antibody techniques as described in Gani et al. J. Steroid Biochem. Molec. Biol. 1994, vol 48, pp. 277–282.

2.1 Preparation of Surfaces

A new carboxy methyl sensor chip (CM5 Biacore AB, Sweden) was docked in a Biacore 2000 Biosensor (Biacore AB, Sweden). The temperature was maintained at 25° C. Flow rate was set at 10 μl/min. The sensor chip surface at flow cell 2 was activated using EDC and NHS activating chemicals from the Biacore AB amine coupling kit by injecting the EDC/NHS mixture into the sample loop and loading 40 μl (marked A on FIG. 2). This was followed by 40 μl 5000 mIU/ml hcg in 10 mM sodium acetate pH3.6 (marked B on FIG. 2). 40 μl 1M ethanolamine was then injected across the surface (marked C on FIG. 2).

2.2 Demonstration of Antibody Unloading from One Surface and Binding to Another

Figure 3:
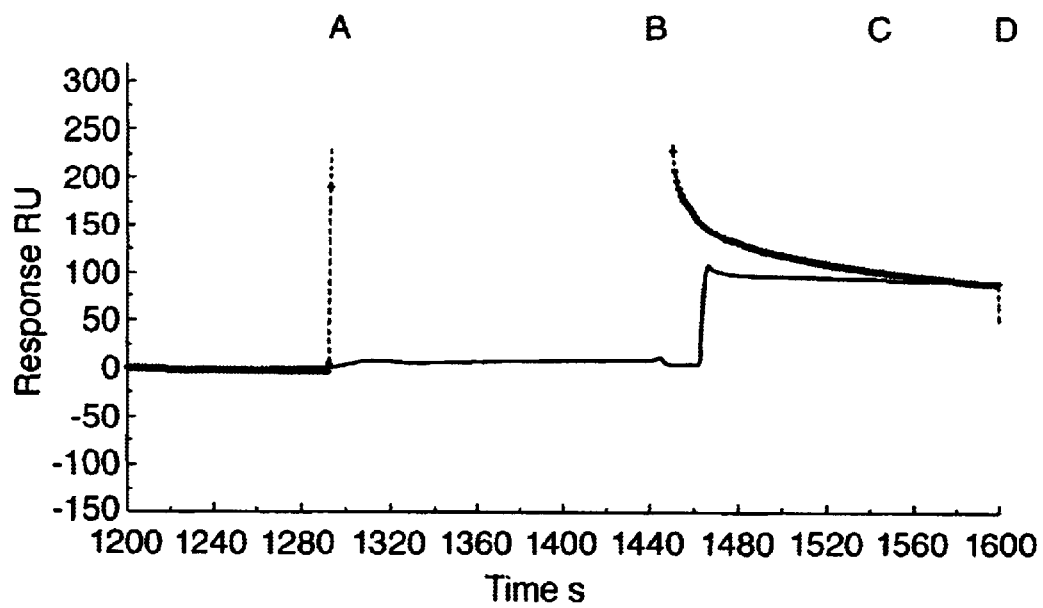
Figure 4:
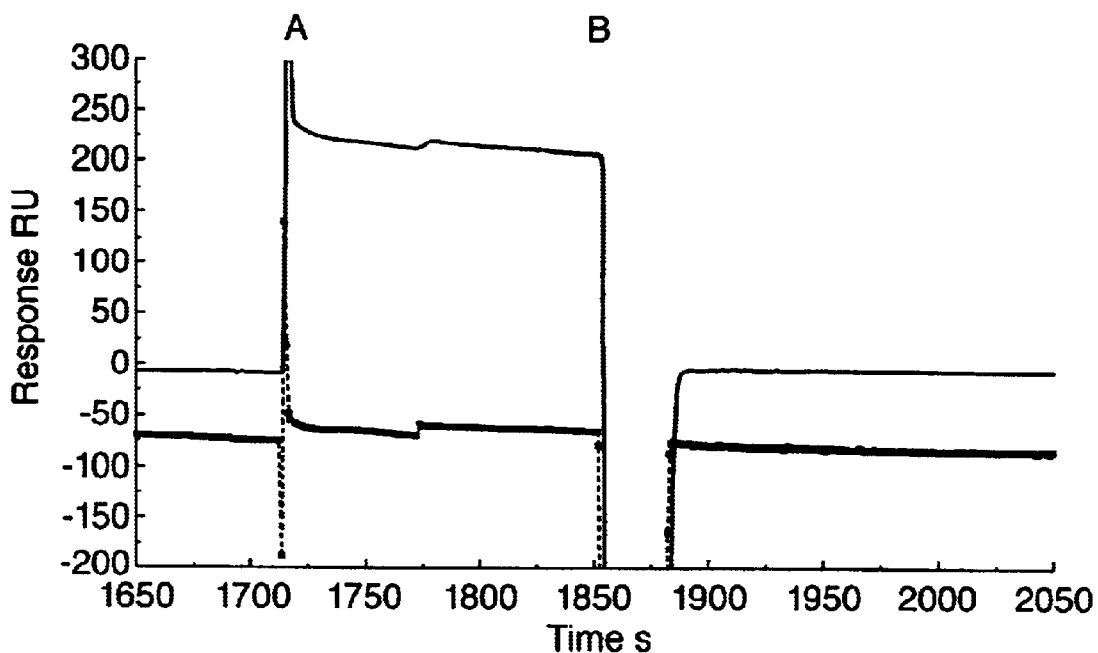

5 μl of 30 μg/ml 3468 was injected in 10 mM sodium acetate pH3.6. The solution was flowed at a rate of 2 μl/min across flow cell 1 (marked A on FIG. 3). Any unbound antibody was washed through the system. When the injection was complete the flow was switched to flow cell 1 and 2 (marked B on FIG. 3) and, therefore, any 3468 that had bound to surface 1 was allowed to bind to surface 2 (marked C on FIG. 3) for about 1 min 25 secs. Antibody was observed coming off of surface 1 and binding to surface 2. Both surfaces were regenerated with the addition of 5 μl 10 mM HCl at 10 μl/min (marked D on FIG. 3). 10 μl of 300 μg/ml 3468 in HBS buffer pH 7.4 was then allowed to flow across both flow cells (marked A on FIG. 4). The antibody only bound to flow cell 2 at this pH. Both surfaces were then regenerated as before with HCl (marked B on FIG. 4).

Figure 5:
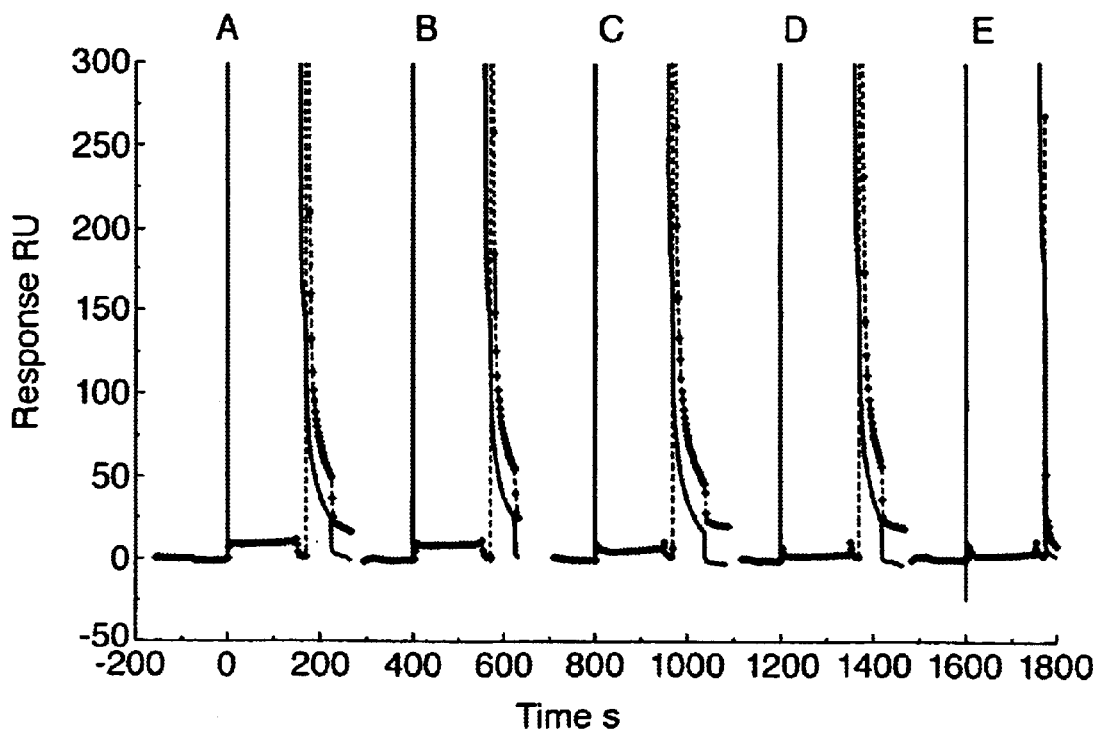

The cycle was repeated to the point of regenerating the chips with HCl (prior to the addition of 3468 in HBS buffer) using 100 mM potassium acetate buffers at pH 4, 6, 7, 8.1, and 8.8 (marked A, B, C, D, and E respectively on FIG. 5) for the initial loading of 3468 on to surface 1. Up to and including pH 8.1, 3468 was observed to come off of surface 1 and bind to surface 2 when the switch in flow pattern was made. At pH8.8 there was no binding of 3468 to surface 2 suggesting that 3468 had not bound to flow cell 1. It can be inferred that the non-specific binding of 3468 with surface 1 is pH dependent and occurring through charge interaction.

In this example, the hcg sensitised surface has a higher affinity for the reagent than the non-sensitised CM5 chip. Therefore, when the second surface is introduced into the system it is able to capture reagent from the first surface and bind to it.

EXAMPLE 3

Experiment to Demonstrate Transfer of Antibody from a Cotton Fabric and Subsequent Specific Binding to a Second Surface.

This example describes the loading of a fabric with an antibody and the subsequent unloading of the antibody, in an aqueous environment, to a surface coated with antigen specific for that antibody. The antibody reagents involved are llama VHH (H115) which specifically recognises hcg, and VHH115 fused to CBD (derived from *Trichoderma reesei*; Linder M., et al, Protein Science, 1995, vol 4, pp. 1056–1064). VHH115 was isolated as described by van der Linden, R (Unique characteristics of llama heavy chain antibodies, 1999, PhD Thesis, University of Utrecht).

1 cm$^2$ pieces of cotton were loaded with 25 μl VHH115-CBD (from 50 μg/ml) in phosphate buffered saline (0.24 g NaH$_2$PO$_4$.H$_2$O, 0.49 g Na$_2$HPO$_2$, 4.25 g NaCl, water to 1 L (pH7.1)) containing 0.15% Tween (PBST). Half of the cotton squares were placed at 37° C. for 30 mins to allow the antibody to dry on to the cotton. The other squares were used wet. Immunotubes (Nunc) were presensitised with 10 μg/ml hcg (Sigma) in bicarbonate buffer (9 ml 0.2M Na$_2$CO$_3$, 16 ml 0.2M NaHCO$_3$) or buffer only. They were then preblocked for 1 hour at 37° C. with 900 μl/tube 1%BSA/PBST. The cotton swatches were placed in the tubes in 900 μl PBST. Incubation was for 1 hour at 37° C. allowing transfer of antibody from the fabric to the hcg coated surface. The cotton squares and PBST were removed from the tubes and binding of VHH115-CBD to hcg was measured using an enzyme linked immunosorbant assay (ELISA). In this instance 900 μl rabbit anti-llama antibody was incubated with the hcg coated surface, at an appropriate dilution in PBST for one hour at 37° C. Any unbound antibody was removed by washing in PBST. This was followed by 900 μl mouse anti-rabbit antibody (Zymed) conjugated to alkaline phosphatase. Incubation was for one hour at 37° C. The tubes were again washed. The level of enzyme conjugated antibody bound to the hcg coated surface was detected via a calorimetric assay after the addition of 900 μl substrate (1 mg/ml pNPP in 1M diethanolamine/1 mM $MgCl_2$). Incubation was for 1.5 hours at room temperature, before 100 μl was removed for reading the optical density OD405 in a microtitre plate reader. The optical density is proportional to the concentration of VHH115-CBD bound to the surface of the immunotube.

Any bound antibody must be derived from the fabric loaded surface. Hence, transfer of an antibody is demonstrated from a fabric to a polystyrene sensitised surface; the affinity of interaction to the specifically sensitised surface being higher than that to the fabric. Furthermore, there is no significant difference between results in which the antibody is not dried on to the cotton and where the antibody is dried so that it has to transfer from the porous structure of cotton. As expected, the specific signals decrease with decreasing concentrations of cotton loaded on the fabric. The results are given in Table 3.

TABLE 3

|  | OD405 vs. Unsensitised tube | Mean | OD405 vs. Hcg sensitised tube | Mean |
| --- | --- | --- | --- | --- |
| μg/ml dried VHH115-CBD |  |  |  |  |
| 50 | 0.052, 0.047 | 0.050 | 0.414, 0.361 | 0.388 |
| 5 | 0.049, 0.055 | 0.052 | 0.113, 0.132 | 0.123 |
| 0.5 | 0.055, 0.052 | 0.054 | 0.048, 0.048 | 0.048 |
| 0 | 0.059, 0.064 | 0.062 | 0.047, 0.049 | 0.048 |
| μg/ml wet VHH115-CBD |  |  |  |  |
| 50 | 0.051, 0.062 | 0.057 | 0.382, 0.457 | 0.420 |
| 5 | 0.055, 0.055 | 0.055 | 0.115, 0.142 | 0.149 |
| 0.5 | 0.062, 0.071 | 0.067 | 0.047, 0.044 | 0.046 |
| 0 | 0.060, 0.067 | 0.064 | 0.047, 0.046 | 0.047 |

The experiment was repeated by loading cotton with either VHH115-CBD or VHHH115 only in order to compare transfer of the same VHH which is either adsorbed non-specifically to cotton or has the ability to bind specifically via CBD. The experiment was performed as described above but only using cotton where the antibody had been dried on to the fabric. The immunotubes were not preblocked. Optical densities were taken after 2.5 hours. Results are shown in Table 4 below.

TABLE 4

|  | OD405 vs. Unsensitised tube | Mean | OD405 vs. Hcg sensitised tube | Mean |
| --- | --- | --- | --- | --- |
| μg/ml VHH115-CBD |  |  |  |  |
| 50 | 0.112, 0.098 | 0.105 | 0.329, 0.368 | 0.349 |
| 5 | 0.062, 0.066 | 0.064 | 0.080, 0.104 | 0.092 |
| 0.5 | 0.071, 0.071 | 0.071 | 0.050, 0.051 | 0.051 |
| 0 | 0.086, 0.073 | 0.08 | 0.050, 0.050 | 0.05 |
| mg/ml VHH115 |  |  |  |  |
| 50 | 0.086, 0.158 | 0.122 | 0.36, 0.331 | 0.346 |
| 5 | 0.067, 0.052 | 0.06 | 0.302, 0.292 | 0.297 |

TABLE 4-continued

|  | OD405 vs. Unsensitised tube | Mean | OD405 vs. Hcg sensitised tube | Mean |
| --- | --- | --- | --- | --- |
| 0.5 | 0.058, 0.06 | 0.059 | 0.055, 0.069 | 0.062 |
| 0 | 0.082, 0.081 | 0.082 | 0.049, 0.048 | 0.049 |

Both anti-hcg VHH and anti-hcg VHH-CBD transfer from cotton to hcg sensitised immunotube in an aqueous environment. For both constructs the affinity for hcg is higher than that for cotton. However, at lower antibody concentrations, there is less binding of VHH115-CBD to hcg, compared to that for VHH115. Since the specificity of the anti-hcg VHH is identical in both constructs, the difference in signals is due to whether the construct is simply adsorbed on to cotton or bound through a specific interaction via CBD. These results, therefore, exemplify loading of antibody bound specifically or non-specifically to a cotton surface, transfer, and specific binding to a polystyrene sensitised surface.

This experiment was repeated using VHH115-CBD, but antibody transfer to hcg took place in 0.2% washing powder OMO base (Na LAS 26%, alkaline silicate 9.53%, STP 26%, $Na_2SO_4$ 12.52%, $Na_2CO_3$ 8.53% in water). Optical densities were taken after 2.5 hours. Results are shown in Table 5.

TABLE 5

|  | OD405 vs. Unsensitised tube | Mean | OD405 vs. Hcg sensitised tube | Mean |
| --- | --- | --- | --- | --- |
| μg/ml VHH115-CBD |  |  |  |  |
| 50 | 0.082, 0.093 | 0.088 | 0.263, 0.271 | 0.267 |
| 5 | 0.087, 0.102 | 0.095 | 0.187, 0.126 | 0.157 |
| 0.5 | 0.098, 0.100 | 0.099 | 0.111, 0.140 | 0.126 |
| 0 | 0.082, 0.071 | 0.077 | 0.198, 0.173 | 0.186 |

Despite background signals to unsensitised tubes being higher than those in previous experiments, the results demonstrate that antibody already loaded on one surface will transfer and bind specifically to a second surface, in an aqueous environment containing washing powder.

EXAMPLE 4

Experiment to Demonstrate Transfer of Antibody from Fabric to SkinA VHH (VHH8) was derived that specifically binds to keratin, the predominant protein of human epidermis.

The antibody has been genetically fused to the protein, human serum albumin (HSA). The substantive deposition of this protein on to skin is likely to confer firming or smoothing benefits. Furthermore, it is known that albumin binds fatty acids in the blood and, therefore, may capture and retain emollient lipids at the skin surface. It is used medically as a healing and soothing agent on burned skin.

In addition, a novel biorecognition molecule incorporating two different antibody specificities and CBD was constructed (anti-RR6-anti-keratin-CBD. In this experiment fabric is loaded with the antibody-fusion reagent. The fabric is then rubbed with a piece of skin and any reagent that has bound to the skin is detected using immunofluorescence.

A fusion protein with specificity for human epidermal keratin, linked to HSA was constructed and produced as follows:

4.1.1 Preparation of a Keratin Specific VHH from Llama

4.1.1.1 Antigen Preparation

Human plantar callus corneocytes were obtained by filing. Soluble callus extract was prepared by suspending 100 mg callus corneocytes in 50 ml 20 mMTris pH7.4/8M urea/1% SDS, boiling for 15 minutes and then sonicating with an ultrasonic probe 22µ for 2 minutes. The sample was centrifuged at 1K×g for 20 minutes at 15° C. The supernatant was recovered and dialysed against PBSa overnight.

4.1.1.2 Immunisation Schedule

A llama, kept at the Dutch Institute for Animal Science and Health (ID-DLO, Lelystad), was immunised with callus corneocytes and subsequently boosted 2 times approximately 1 month apart. The serum used for library construction was removed 1 week after the second boost.

4.1.1.3 Polyclonal Sera Analysis

Sera were analysed by ELISA against callus soluble extract as follows:

1. Sterilin microtitre plate (Sero-Wel) was sensitised with 100 µl/well 25 µg/ml callus extract in PBSa. Plates were incubated overnight at 4° C. and then washed in PBSa.
2. The plate was blocked by preincubating with 200 µl/well 1% marvel in PBSTa for 1 hour at 37° C.
3. Blocking buffer was removed and 100 µl/well llama immunised sera or prebleed, beginning with a $10^{-1}$ dilution in PBSa, added. Incubations were for 1 hour at 37° C.
4. Unbound antibody fragment was removed by washing 4× using a plate washer in PBSTa.
5. 100 µl/well of rabbit anti-llama VHH was added at an appropriate dilution in PBSTa. Incubation was for 1 hour at 37° C.
6. Plate was washed as described in step 3.
7. 100 µl/well alkaline phosphatase conjugated goat anti-rabbit (Jackson) was added at an appropriate dilution in PBSTa and incubated for 1 hour at 37° C.
8. Plate was washed as described previously.
9. Alkaline phosphatase activity was detected by adding 100 µl/well substrate solution: 1 mg/ml pNPP in 1M diethanolamine, 1 mM $MgCl_2$.
10. Absorbance was read at 405 nm when the colour had developed.

4.1.1.4 mRNA Isolation and cDNA Synthesis $2.5 \times 10^8$ peripheral blood lymphocytes (PBLs) were isolated using a ficoll gradient. RNA was isolated based on the method of Chomczynnski and Sacchi, (1997) Anal. Biochem., vol 162, pp 156–159. mRNA was subsequently prepared using Oligotex mRNA Qiagen Purification kit.

cDNA was synthesised using First Strand Synthesis for RT-PCR kit from Amersham (RPN 1266) and the oligo dT primer. Approximately 2 µg mRNA was used (100 µg/Eppendorf) as estimated from the total RNA concentration and assuming that mRNA constitutes 1% of the total RNA.

4.1.1.5 Isolation of Short and Long-hinge VHHs by PCR

A master mix for the amplification of short and long-hinge PCR was prepared as follows:

46 µl dNTP mix (5 mM)

11.5 µl LAM 07 or LAM 08 (100 pmol/µl)

LAM 07: 5' AACAGTTAAGCTTCCGCTTGCGGCCGCG-GAGCTGGGGTCTTCGCTGTGGTGCG

LAM 08: 5' AACAGTTAAGCTTCCGCTTGCGGC-CGCTGGTTGTGGTTTTGGTGTCTTGGGTT 11.5 µl VH2B (100 pmol/µl)

VH2B: 5' AGGTSMARCTGCAGSAGTCWGG

S=C/G, M=A/C, W=A/T, R=A/G

115 µl $MgCl_2$ (25 mM)

161 µl dep water 0.20 tubes for both short and long-hinge amplification were prepared containing 15 µl/Eppendorf of the above master mix and 1 ampliwax (Perkin Elmer). Tubes were incubated for 5 minutes at 75° C. to melt the wax and then placed on ice. 35 µl of the following appropriate mix was added to each Eppendorf:

200 µl 5×stoffel buffer (Perkin Elmer)

20 µl Amplitaq DNA polymerase stoffel fragment (Perkin Elmer)

1140 µl dep water

40 µl cDNA

Negative controls had the cDNA omitted and replaced with dep water.

The reactions conditions were:

1 cycle at
    94° C. 5 minutes
    {94° C. 1 minute
35 cycles at
    {55° C. 1.5 minutes
    {77° C. 2 minutes
1 cycle at
    72° C. 5 minutes Identical reactions were pooled and 5 µl was analysed on a 2% agarose gel.

4.1.1.6 Restriction Enzyme Digestion of VHHs and pUR4536

Figure 6:
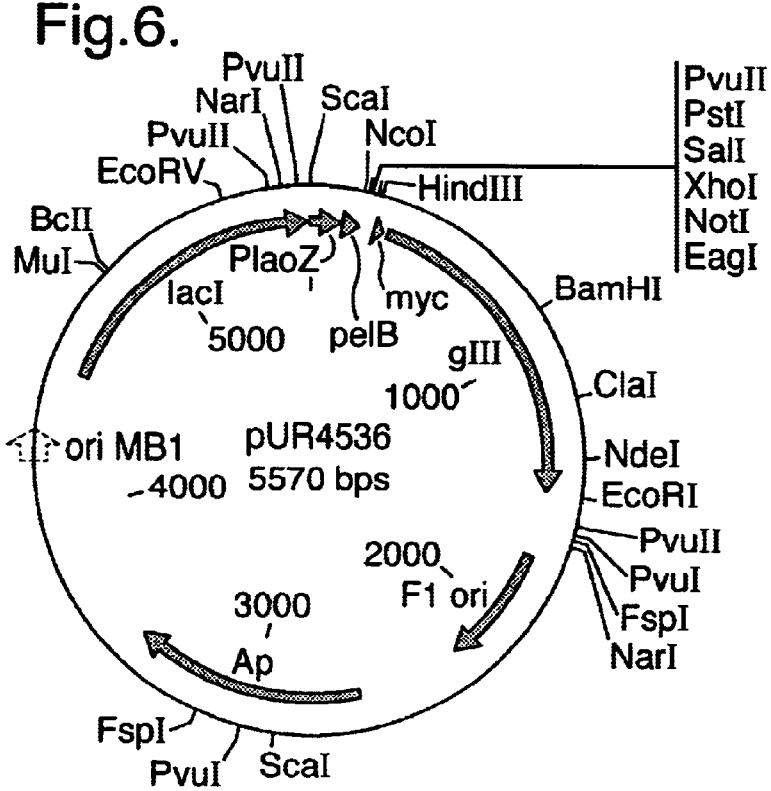

Pooled llama short and long-hinge PCR products were purified from a 2% agarose gel using Qiaex II purification kit (Qiagen) and resuspended in a final volume of 80 µl. 40 µl of this sample was digested using Hind III and Pst1 (Gibco BRL) according to manufacturer's instructions. Digested PCR products were again purified as detailed above. pUR4536 (FIG. 6) was similarly digested and purified.

4.1.1.7 Generation of Short and Long-hinge VHH Libraries

Appropriate ratios of PCR product were combined with digested vector using DNA ligase (Gibco BRL) according to manufacturer's instructions. Ligation reactions were purified and used to transform electrocompetent E. coli JM109.

4.1.1.8 Phage Rescue Maxiscale 15 ml 2TY/Amp/Glucose (16 g Tryptone, 10 g yeast extract, 5 g NaCl per liter, containing 2% glucose and 100 µl g/ml ampicillin) was inoculated with 100 µl of glycerol stock of either short or long-hinge VHH library and phage rescues were performed. The cells were grown until log phase was reached and infected with M13K07 helper phage (Gibco BRL). Infected cells were pelleted and resuspended in 2TY/Amp/Kan to allow release of phage into the supernatant. After overnight incubation at 37° C., phage were pelleted and concentrated by PEG precipitation. The final phage pellet was resuspended in 3 ml PBS in 2% BSA/1% marvel and incubated for approximately 30 minutes at room temperature.

4.1.1.9 Selection of Antigen Binding Phages: Panning

Nunc-immunotubes were sensitised with either 1 ml of 50 µg/ml soluble callus extract in PBSa, or PBSa only (as a negative control) overnight at 4° C. The tubes were washed with PBSa and preblocked with 2 ml 2% BSA/1% marvel in PBSTa at room temperature for about 3 hours. Blocking solution was removed and 1 ml of blocked phage solution was added to the immunotubes. Samples were incubated for 4 hours at room temperature. The tubes were washed 20× with PBST and 20× with PBS Bound phage were removed with 0.5 ml 0.2M glycine/0.1M HCl pH2.2 containing 10 mg/ml BSA, and incubating at room temperature for 15 minutes. The solution was removed into a fresh tube and neutralised with 30 μl 2M Tris. 200 μl 1M Tris pH7.5 was added to both the tubes and biopsy skin.

The eluted phage were added to 9 ml log-phase *E. coli* XL-1 Blue. 4 ml log-phase *E. coli* was also added to the immunotubes and biopsy skin. Cultures were incubated for 30 minutes at 37° C. without shaking to allow for phage infection of the *E. coli*.

The cultures were pooled as appropriate, pelleted, resuspended in 2TY and plated out on SOBAG plates (20 g bact-tryptone, 5 g bacto-yeast extract, 0.5 g NaCl per liter, 10 mM $MgCl_2$, 1% glucose, 100 μg/ml ampicillin) for harvesting and the panning process was repeated a further 2 times.

4.1.1.10 Generation of Soluble VHH Fragments

Clones from the panned libraries were harvested and DNA was isolated from the cell pellets using Qiagen midi-prep kit. DNA from each panned library was used to transform $CaCl_2$ competent *E. coli* D29A1, which were plated out on SOBAG plates and grown overnight at 37° C. Individual colonies of freshly transformed *E. coli* D29A1 were picked and VHH expression induced on a microtitre plate scale using IPTG.

4.1.1.11 Detection of Expression of Anti-Skin VHH-myc Constructs

Sterilin microtitre plate (Sero-Wel) was sensitised with either callus soluble extract or PBSa only. Plates were blocked with 200 μl/well 1% BSA/PBSTa for 1 hour at 37° C. 90 μl crude *E. coli* supernatant was premixed with 45 μl 2% BSA/PBSa and added to the appropriate wells of the blocked plates. Incubation was for 2 hours at 37° C. Unbound fragment was removed by washing 4x with PBSTa. 100 μl/well of an appropriate dilution of mouse anti-myc antibody (in house) in 1% BSA/PBSTa was added and incubated for 1 hour at 37° C. Plates were washed as previously and 100 μl/well of an appropriate dilution of alkaline phosphatase conjugated goat anti-mouse (Jackson) in 1% BSA/PBSTa added and incubated as before. Plates were again washed and alkaline phosphatase activity was detected by adding 100 μl/well substrate solution: 1 mg/ml pNPP in 1M diethanolamine/1 mM $MgCl_2$. When the colour had developed an absorbance reading at 405 nm was taken. The clone VHH8 was identified as specifically binding to epidermal keratin.

4.1.2 Isolation of the HSA Gene by PCR and Construction of $VHH8_2$-HSA

HSA was amplified from the genomic DNA of Pichia pastoris via PCR. Two oligonucleotide primer pairs were used to amplify the DNA and introduce restriction sites allowing cloning. Primer pair one (SW21 and SW22), allowed C-terminal fusions of HSA with antibody fragments. Primer pair 2 (SW23 and PCR392) enabled the engineering of constructs fused via the N-terminus of HSA.

SW21: CACCTGGGCCATGGCCGGCTGGGC-CCCTAAGCCTAAGGCAGCTTGACTTGCAG

SW22: GGGCTTGATTGGAGCTCGCTCATTCC

SW23: GCAGGATCCGATGCACACAAGAGTGAGGTTGC

PCR392: GCAAATGGCATTCTGACATCC

The C terminus construct (HSA-VHH8) was ligated into pPic9 as a three point ligation with VHH8 possessing 5' Sfi 1 and 3' EcoR1 restriction enzyme sites, according to standard molecular biology techniques.

Figure 7:
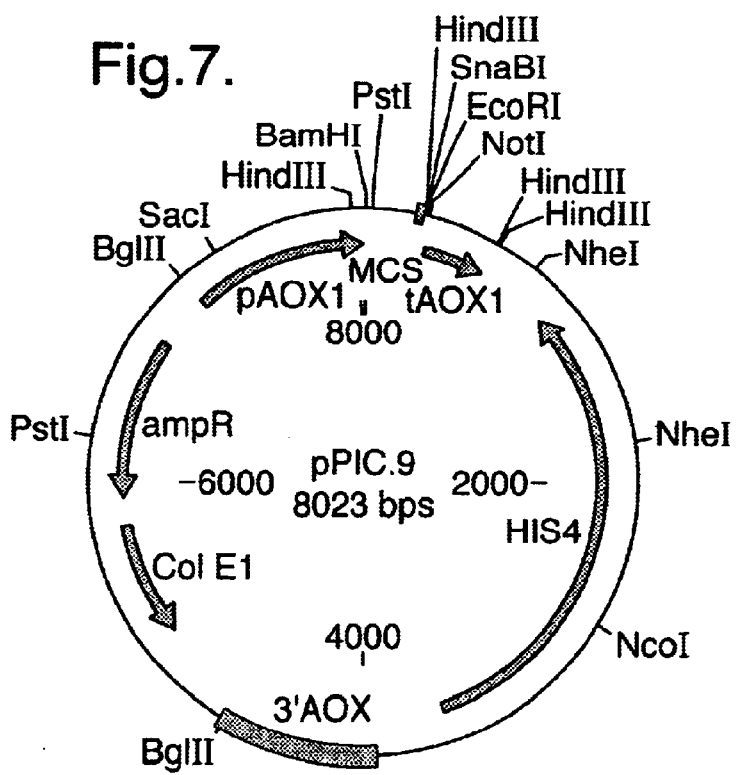

The N-terminus construct (VHH8-HSA) was ligated into pPic9 (FIG. 7) as a four point ligation into pPic9 digested with Sac1/EcoR1:—Aox gene as Sac1/Xho1, VHH8 as Xho1/BamH1, and HSA as a BamH1/EcoR1 fragment. This was performed using standard molecular biology techniques.

$VHH8_2$-HSA was constructed by manipulation of the N and C terminal constructs. The C terminal construct was digested with Xba1/EcoR1, and the N terminal construct was digested with Sac1/Xba1. These fragments were ligated with pPic9 that had been digested with Sac1/EcoR1. The DNA sequence is shown in FIG. 8.

4.1.2.1 Expression of $VHH8_2$-HSA in *P. pastoris* pPic9 vector containing $VHH8_2$-HSA fusion construct was transformed into the methylotrophic yeast, *P. pastoris* GS115. 10 μg vector DNA was digested with the DNA restriction enzyme Bgl II, purified and used to transform electrocompetent *P. pastoris* strain GS115 (Invitrogen) according to manufacturer's instructions. Expression of the fusion construct was induced by the addition of methanol. Supernatants were harvested by centrifugation and analysed. Protein was purified via the histidine tail and nickel NTA.

4.2 Generation of Anti-RR6-VHH8-CBD

Anti-keratin VHH8 was prepared as described above.

4.2.1 Preparation of Anti-RR6 Specific VHH from Llama

Anti-RR6 VHH was isolated similarly to that of anti-keratin VHH, as described by Linden, R (Unique characteristics of llama heavy chain antibodies, 1999, PhD Thesis, University of Utrecht). It binds the azo-dye reactive red 6 (RR6).

4.2.2 Construction of Anti-RR6-anti-keratin-CBD

Anti-RR6VHH was genetically fused to 6 histidines (for purification purposes) and CBD derived from *Trichoderma reesei* (Linder M. et al., Protein Science, 1995, vol 4, pp. 1056–1064), and cloned into pPic9 (Appendix 2). VHH8 (anti-keratin) was subsequently isolated from pur4536 by restriction enzyme digestion. Using BstEII, VHH8 was ligated between the anti-RR6 VHH and CBD sequence in pPic9. The DNA sequence is shown in FIG. 9.

4.2.3 Production and Analysis of Anti-RR6-VHH8-CBD

Approximately 2–5 μg DNA in 2 μl $H_2O$ (TthIIIi, SacI digested) pPic constructs was used to transform *P. pastoris* GS115 cells as described 4.1.2.1

4.2.4 Production and Evaluation of Anti-RR6-VHH8-CBD

Transformed and selected *P. pastoris* clones were induced to express antibody using the protocol outlined below:

1) Using a single colony from the MD plate, inoculate 10 ml of BMGY (1% Yeast Extract, 2% Peptone, 100 mM potassium phosphate pH6.0, 1.34% YNB, 4×1 0–5% Biotin, 1% Glycerol) in a 50 ml Falcon tube.
2) Grow at 30° C. in a shaking incubator (250 rpm) until the culture reaches an OD600~2–8.
3) Spin the cultures at 2000 g for 5 minutes and re-suspend the cells in 2 ml of BMMY medium (1% Yeast Extract, 2% Peptone, 100 mM potassium phosphate pH6.0, 1.34% YNB, 4×10–5% Biotin, 0.5% Glycerol).
4) Return the cultures to the incubator.
5) Add 20 μl of MeOH to the cultures after 24 hours to maintain induction.
6) After 48 hours harvest the supernatant by removing the cells by centrifugation.

The crude supernatants were tested for the presence of antibody construct via analysis on 12% acrylamide gels using the Bio-Rad mini-Protean II system. VHH8 activity was detected as described section 4.1.1.11. Results are shown in FIG. 10.

Anti-RR6 Activity was Detected as Follows 1) 96 well ELISA plates (Greiner HB plates) were sensitised overnight at 37° C. with 100 µl/well of BSA-RR6 conjugate (azo-dye R6 (ICI) which was coupled to BSA via its reactive triazine group) in PBS or PBS only.
2) Following one wash with PBST the wells were incubated for 1 hour at 37° C. with 100 µl blocking buffer (1% BSA in PBST) per well.
3) Test supernatants (50 µl) were mixed with equal volumes of blocking buffer and added to the sensitised ELISA wells. Incubated at 37° C. for 1 hour.
4) Following 4 washes with PBST, 100 µl rabbit anti-llama polyclonal sera (in house) was added at an appropriate dilution in blocking buffer. Incubated at 37° C. for 1 hour.
5) Following four washes with PBST, goat anti-rabbit conjugated to alkaline phosphatase (Zymed) was added at an appropriate dilution in blocking buffer. Incubated at 37° C. for 1 hour.
6) After washing 4 times with PBST, 100 µl/well pNPP substrate (1 mg/ml pNPP in 1M diethanolamine/1 mM $MgCl_2$) was added to each well. When colour had developed, plates were read at 405 nm. Results are shown in FIG. 10.

CBD Binding Activity was Detected as Follows 1) 20 µl 1% ethylcellulose and 80 µl 0.1% marvel in PBST (blocking buffer), or blocking buffer only, were added to wells of an MAHV 0.45µ filter plate (Millipore). Incubated for 1 hour at room temperature with shaking.
2) Buffer was removed using a vacuum manifold
3) Test supernatants (50 µl) were mixed with equal volumes of blocking buffer and added to the ELISA wells. Incubated at room temperature for 1 hour, with shaking.
4) Following 10 washes with PBST, 100 µl rabbit anti-llama polyclonal sera (in house) was added at an appropriate dilution in blocking buffer. Incubated at room temperature for 1 hour, with shaking.
5) Following 10 washes with PBST goat anti-rabbit conjugated to alkaline phosphatase (Zymed) was added at an appropriate dilution in blocking buffer. Incubated at room temperature for 1 hour, with shaking.
6) After washing 10 times with PBST, 100 µl/well pNPP substrate (1 mg/ml pNPP in 1M diethanolamine/1 mM $MgCl_2$) was added to each well. When colour had developed, substrate was removed to a new solid ELISA plate and optical density was measured at 405 nm. Results are shown in FIG. 10.

4.2.5 Large Scale Expression of Construct

The clone giving the best expression levels and binding activities was selected and produced on 3 L fermentation scale in a fermenter. Purification was via the histidine tail using IMAC (Immobilised metal affinity chromatography).

4.3 Demonstration of $VHH8_2$-HSA and Anti-RR6-VHH8-CBD Binding to Fabric and Subsequent Transfer to Skin 50 µl of 50 µg/ml $VHH8_2$-HSA, anti-RR6-VHH8-CBD, or PBST only was loaded on to 1 $cm^2$ pieces of cotton fabric. 0.5 $cm^2$ pieces of human biopsy facelift skin was prepared and glued, epidermal side uppermost, onto the surface of glass microscope slides using a drop of super glue. Samples were encircled with Pap-pen to prevent solutions from spreading too far. The biopsies were rinsed thoroughly in distilled water followed by PBST and left to drain for a few minutes. The antibodies were transferred from the fabric to the skin by rubbing the two together, in the presence of 50 µl PBST, for a 2 minute period using a circular motion with the index finger of a latex gloved hand. Subsequent binding of the reagents to skin was demonstrated via immunofluorescence. The identical procedure was performed for biopsy skin that had not come into contact with the genetic fusions. Also binding of antibody to cotton that was not rubbed on to skin, or skin that was not rubbed with cotton, was performed. Rabbit anti-llama VHH (in-house) antibody, at an appropriate dilution, was pipetted onto the surface of the skin and incubated for 1 hour at room temperature. Any unbound material was removed by washing the skin vigorously in PBST. Binding was then detected via anti-rabbit antibody conjugated to FITC (Jackson) at an appropriate dilution. Incubation was for 1 hour at room temperature. Again, any unbound conjugate was removed by washing in PBST. Bound conjugate was visualised using a Bio-Rad MRC600 Confocal Scanning Laser Microscope (Bio-Rad Laboratories Ltd), attached to an Ortholux II microscope (Leica Microsystems UK Ltd), with 488 nm laser excitation. A Nikon Fluor 20/0.75 PhsDL was used with a zoom factor of 1.0 to image the slides. Two representative areas of each sample were recorded. The black and gain levels for each set of images were set up using the negative control and then kept constant for the remainder of the samples. The Bio-Rad CoMos software was used to capture, store, and analyse the images. The sites of fluorescence indicate where the genetic fusion has bound to the skin. Any bound material will have been derived from fabric, transferred to the skin by rubbing, and bound through specific interaction.

Representative images are shown in FIG. 11. This example demonstrates the transfer of an antibody and an antibody genetically fused to the benefit agent HSA from fabric to skin. Images of cotton (H), or skin (I), or skin that has been rubbed with cotton, but not exposed to antibody (G), show only very low levels of autofluorescence. Anti-RR6-VHH8-CBD binds specifically to cotton (C) or skin (E) showing high levels of fluorescence. For skin, the individual squames are clearly delineated. Similarly $VHH8_2HSA$ binds specifically to skin (F). But, after the numerous steps required for detection, no non-specific antibody binding to cotton was detected (D). Images A and B clearly demonstrate that both antibody constructs (with or without benefit agent) have been transferred from cotton to skin since individual squames are fluorescently outlined. For both constructs, binding to skin is via specific interaction with VHH8. Binding to cotton is specific for anti-RR6-VHH8-CBD via CBD, and non-specific for $VHH8_2HSA$.

EXAMPLE 5

Experiment to Demonstrate Binding of Oil Bodies to Cotton, and Subsequent Transfer and Binding to Skin. Delivery of benefit agent encapsulated in a particle is exemplified by the use of oil bodies which have been prepared containing the lipophilic regent, nile red, which also acts as a fluorescent label. Targeted delivery and transfer from cotton to skin was demonstrated using the novel biorecognition molecule anti-RR6-VHH8-CBD. This molecule was constructed with the aim of being able to specifically deposit particles, sensitised with the azo-dye RR6, to cotton via CBD, and/or skin via anti-keratin VHH8. The molecule was constructed as described in Example 4.

5.1 Oil Body Isolation

Oil bodies were isolated from rape seeds essentially as described by Tzen et al (J.Biol.Chem., 1992, vol 267, pp. 15626–15634). Briefly rape seeds were ground to a fine powder in liquid nitrogen using a pestle and mortar, and sieved. 1 g crushed seed was homogenised in 4 g grinding medium, on ice. The sample was mixed with an equal volume of floating medium containing 0.6M sucrose, and centrifuged. The 'fat pad' was removed to another tube, resuspended in floating medium containing 0.25M sucrose, and centrifuged. The 'fat pad' was collected and stored at 4° C.

5.2 Preparation of Oil Bodies Containing Nile Red

In order to be able to visualise the presence of oil bodies on skin or cotton, they were prepared containing the lipophilic reagent, nile red, which also acts as a fluorescent label.

Figure 12:
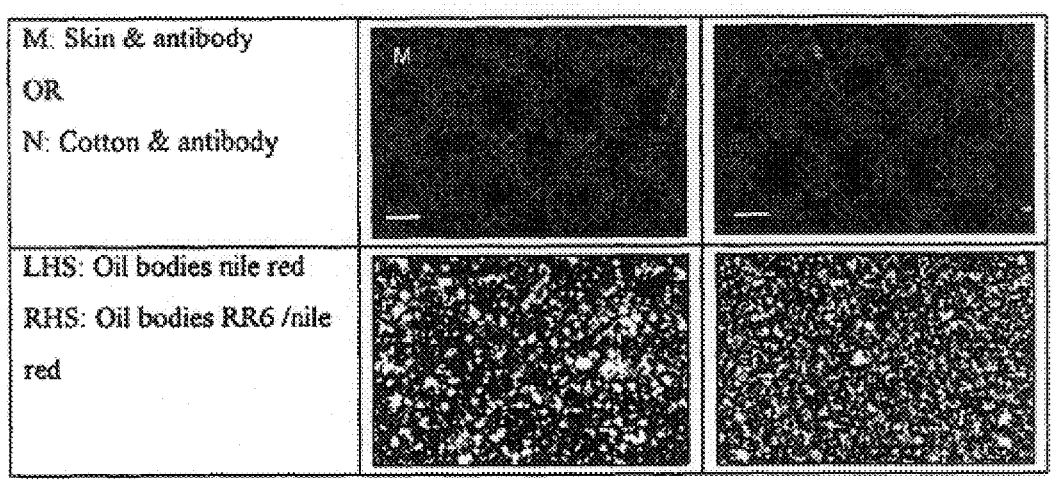

A crystal of nile red was added to a 2% suspension of oil bodies in water. The sample was vortexed for 2 minutes and centrifuged at 13,000 rpm for 2 minutes. The upper layer containing the oil bodies was removed and washed with PBS 3 times. After the final wash, the oil bodies were resuspended in 5 ml PBS. An image of these oil bodies is shown in FIG. 12.

5.3 Sensitisation of Oil Bodies with Reactive Red 6 and Nile Red

An antibody able to bind RR6 was available, therefore, oil bodies was sensitised with RR6 in order to be able to study specific deposition of oil bodies to surfaces.

0.1 g oil bodies were resuspended in 4.8 ml 0.1M $Na_2B_4O_7.10H_2O$, 0.05M NaCl pH8.5, and 0.2 ml 2% RR6 (ICI) in water. The suspension was rotated overnight at room temperature. The sample was centrifuged at 13000 rpm for 2 minutes, and the upper layer removed and nile red added as described above. An image of these oil bodies is shown in FIG. 12.

5.4 Delivery of Oil Bodies to Skin from Cotton 1 cm² squares of cotton were placed in 3 ml volume glass vials. The cotton was prewashed for 30 minutes in 1 ml PBST with shaking.

In the first step, the buffer was decanted and replaced with 1 ml of 25 µg/ml anti-RR6-VHH8-CBD in PBST, or PBST only. Incubation was for 1 hour at room temperature with shaking. The samples were washed 3×5 minutes with 1 ml PBST, shaking at room temperature. Samples were then incubated for 1 hour, room temperature, with shaking, with either of the following:

100 µl oil bodies containing nile red and 900 µl PBST

100 µl oil bodies containing nile red, sensitised with RR6 and

900 µl PBST 1 ml PBST only.

Meanwhile, 0.5 cm² human biopsy facelift skin was prepared and glued, epidermal side uppermost, on to the surface of a glass microscope slide using a drop of superglue. Samples were encircled with Pap-Pen to prevent solutions from spreading too far. The skin was then rinsed in distilled water followed by PBST and allowed to drain for a few minutes.

In the second step, the skin was rubbed with the cotton for 2 minutes with a gentle circular motion using the index finger of a latex gloved hand. The skin samples were washed vigorously in a bath of PBST.

As additional controls, cotton was prepared as previously described but not rubbed on to skin, in order to visualise level of binding of oil bodies prior to rubbing. Also, binding of oil bodies directly to skin, without being rubbed with cotton, was determined by incubating skin for 10 minutes with antibody or PBST. The skin was washed vigorously in a bath of PBST. Oil body samples were then pipetted directly on to the skin and incubated for 10 minutes at room temperature, after which the skin was again washed vigorously in a bath of PBST.

All samples, including cotton after being rubbed on to skin (to determine level of oil bodies remaining on cotton), were visualised using a Bio-Rad MRC600 Confocal Scanning Laser Microscope (Bio-Rad Laboratories Ltd), attached to an Ortholux II microscope (Leica Microsystems UK Ltd), with 488 nm laser excitation. A Nikon Fluor 20/0.75 PhsDL was used with a zoom factor of 1.0 to image the slides. Two representative areas of each sample were recorded. The black and gain levels for each set of images were set up using the negative control and then kept constant for the remainder of the samples. The Bio-Rad CoMos software was used to capture, store, and analyse the images. Representative images are shown in FIG. 11.

Figure 13:
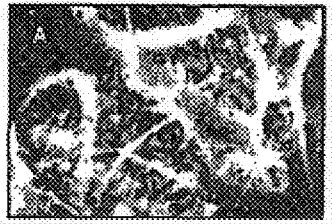
Figure 14:

Cotton (N) or skin (M) which had only been incubated with antibody, showed very low levels of autofluorescence. The sample in which oil bodies sensitised with RR6, were captured by antibody on skin (I) or cotton (J), showed very high levels of all over deposition. For skin, individual squames were clearly delineated. When RR6 sensitised oil bodies were first captured by cotton through specific interaction and then rubbed on to skin in the second step, there was a good coverage of deposition on skin (A) with some areas being more densely covered than others. This demonstrates, surprisingly, that oil bodies can be specifically captured on cotton in the presence of detergent and then transferred to skin after 2 minutes of rubbing. There was a lot of oil bodies left on the cotton (B) after rubbing although less than that where cotton was not rubbed on to skin (J) i.e giving an indication of the proportion of antibody transferred. Even without the presence of antibody for specific capture and transfer of oil bodies, an even deposition of RR6 sensitised oil bodies (C) on skin was achieved. Oil bodies containing nile red but not sensitised with RR6 (i.e unable to be specifically targeted via antibody) could be deposited non-specifically to cotton (L, F) but only low levels of fluorescence were visible on skin (K, E). Therefore, surprisingly, particles can bind non-specifically to surface 1 and transfer and bind non-specifically to surface 2.

Using anti-RR6-VHH8-CBD has allowed sensitised oil bodies to be targeted specifically to cotton and skin and resulted in more substantive deposition of encapsulated material to skin after being transferred from cotton.

EXAMPLE 6

Experiment to Demonstrate Binding of Antibody and Oil Bodies to Cotton in the Presence of Washing Powder, and Transfer to Skin. Specific Binding Compared using Anti-RR6-VHH8-CBD or Anti-RR6 only.

Deposition of antibody and capture of oil bodies to cotton in the presence of either PBST or the washing powder, OMO base, was compared. An additional aim was to exemplify that the anti-keratin VHH8, despite being bound to cotton in step 1 as part of the anti-RR6-VHH8-CBD reagent, was aiding in providing more substantive deposition of particles to skin when skin was rubbed with cotton which had been pre-prepared with antibody and particles.

The experimental methodology was as described for Example 5 using only oil bodies sensitised with RR6, and either anti-RR6 VHH or anti-RR6-VHH8-CBD. Both antibodies and oil bodies were captured on cotton in the presence of PBST (pH7.1) or 0.2% OMO base (Na LAS 26%, alkaline silicate 9.53%, STP 26%, $Na_2SO_4$ 12.52%, $Na_2CO_3$ 8.53%) in distilled water.

Representative images of oil body deposition in the presence of PBST or OMO are shown in FIGS. 13 and 14 respectively. As well as deposition of oil bodies to skin after rubbing with skin, images are also shown of the cotton swatches after rubbing showing the relative levels of oil bodies remaining bound to cotton. Images of skin (I) or cotton (J) after being rubbed with cotton incubated with antibody only, show very low levels of background autofluoresence. As in Example 5, RR6 sensitised oil bodies can be captured non-specifically to cotton and deposited on to skin (E, F). However, use of antibodies greatly enhances the level of deposition of particles finally achieved on skin. Oil bodies captured on cotton in the presence of PBST, show similar levels of deposition on skin after rubbing whether anti-RR6-CBD (FIG. 13, C) or anti-RR6-VHH8-CBD (FIG. 13, A) is used. However, if 0.2% OMO is used for capturing oil bodies to cotton, then using anti-RR6-VHH8-CBD results in a visible increase in the level of deposition of oil bodies to skin (FIG. 14, A) compared to if just anti-RR6-CBD (FIG. 14, C) is used. This is further supported by the evidence that less fluoresence is left on cotton after rubbing on skin if anti-RR6-VHH8-CBD is used (B) compared to anti-RR6-CBD only (D). This is independent of whether PBST (FIG. 13) or OMO (FIG. 14) is used, although differences in deposition levels on skin are only visible if OMO is used. This exemplifies that, surprisingly, all three specificities of the novel biorecognition molecule anti-RR6-VHH8-CBD are functional. In addition, using this molecule provides an advantage in enabling particles to be deposited specifically to fabric in step 1, and subsequent transfer and binding to skin, in step 2, if washing powder is present in step 1 of the process.

What is claimed is:

1. A method of delivering a benefit agent whereby a benefit agent is loaded to a first surface by contacting the first surface with a binding molecule carrying the benefit agent and subsequently unloaded and transferred and delivered to a second surface wherein said binding molecule is selected from the group consisting of an antibody, an antibody fragment and a derivative thereof.

2. Method according to claim 1, whereby the benefit agent is first loaded onto a garment during a laundering process, and subsequently delivered to the second surface.

3. Method according to claim 1, wherein said benefit agent is a laundry benefit agent selected from the group consisting of fragrance agents, perfumes, colour enhancers, fabric softening agents, polymeric lubricants, photoprotective agents, latexes, resins, dye fixative agents, encapsulated materials, antioxidants, insecticides, soil repelling agents, soil release agents, and cellulose fibers.

4. Method according to claim 1, wherein said benefit agent is a skin benefit agent selected from the group consisting of bleach, moisturisers, skin softeners (e.g. silicones), emollients, sunscreens, lipids, vitamins, anti-microbial agents, anti-aging benefits, anti-perspirants, skin lightening agents, and chemicals.

5. Method according to claim 1 to deposit a skin care benefit agent to skin, wherein the binding molecule is selected from the group consisting of an antibody complex, or protein-antibody complex, that binds to fabric.

6. Method according to claim 1, wherein the first surface is fabric and the second surface is skin.

7. Method according to claim 6 wherein the binding molecule is selected from the group consisting of antibodies and protein derivatives the method resulting in removal of unwanted components from the skin.

8. A method of delivering a benefit agent whereby a benefit agent is loaded to a first surface by contacting the first surface with a binding molecule carrying the benefit agent and subsequently unloaded and transferred and delivered to a second surface wherein said binding molecule is a fusion protein comprising a cellulose binding domain and a domain having a high binding affinity to another ligand.

9. A method of delivering a benefit agent whereby a benefit agent is loaded to a first surface by contacting the first surface with a binding molecule carrying the benefit agent and subsequently unloaded and transferred and delivered to a second surface wherein said benefit agent is an enzyme or enzyme part capable of catalyzing the formation of a bleaching agent.

10. Method according to claim 1, wherein said benefit agent is an oxidase or haloperoxidase.

11. A method of delivering a benefit agent whereby a benefit agent is loaded to a first surface by contacting the first surface with a binding molecule carrying the benefit agent and subsequently unloaded and transferred and delivered to a second surface wherein said benefit agent is selected from the group consisting of glucose oxidase, galactose oxidase alcohol oxidase and chloroperoxidase.

12. Method according to claim 11, wherein said benefit agent is a vanadium chloroperoxidase.

13. Method according to claim 12, wherein said benefit agent is a *Curvularia inaequalis* chloroperoxidase.

14. Method according to claim 9, wherein said bleaching agent is hydrogen peroxide or a hypohalite.

15. Method of claim 9, wherein said enzyme part is a laccase or a peroxidase and said bleaching agent is derived from an enhancer molecule that has reacted with the enzyme.

16. The method of claim 9, wherein said enzyme part is bound to said binding molecule having a high binding affinity for porphyrin derived structures, tannins, polyphenols, carotenoids, anthocyanins, and Maillard reaction products.

17. The method of claim 9, wherein said enzyme part is bound to said binding molecule having a high binding affinity for porphyrin derived structures, tannins, polyphenols, carotenoids, anthocyanins, and Maillard reaction products when they are adsorbed onto the surface of a fabric.

18. The method of claim 1, wherein the first surface is a fabric selected from the group consisting of cotton, polyester, polyester/cotton, and wool.

19. A method of delivering a benefit agent whereby a benefit agent is loaded to a first surface by contacting the first surface with a binding molecule carrying the benefit agent and subsequently unloaded and transferred and delivered to a second surface wherein second surface is selected from the group consisting of fabric skin, and a ligand.

20. Method according to claim 1, wherein said antibody or said antibody fragment or said derivative thereof is all of part of a heavy chain immunoglobulin that was raised in Camelidae and has a specificity for stain molecules.

21. Method according to claim 1, wherein said antibody or said antibody fragment or said derivative thereof bind to chemical constituents which are present in tea, blackberry and red wine.

22. Method according to claim 19, wherein said ligand binds to chemical constituents which are present in tea, blackberry and red wine.

23. A method of delivering a benefit agent whereby a benefit agent is loaded to a first surface by contacting the first surface with a binding molecule carrying the benefit agent and subsequently unloaded and transferred and delivered to a second surface wherein the binding molecule has a chemical equilibrium constant $K_d$ for the first surface of less than $10^{-4}$ M.

24. Method according to claim 23, wherein the binding molecule has a chemical equilibrium constant $K_d$ for the first surface of less than $10^{-7}$ M.

* * * * *